US012758485B2

(12) United States Patent
Frushour et al.

(10) Patent No.: US 12,758,485 B2
(45) Date of Patent: Oct. 13, 2026

(54) INSTANT EFFECT EYE CREAM

(71) Applicant: Mary Kay Inc., Addison, TX (US)

(72) Inventors: Michael Frushour, Addison, TX (US); David Gan, Southlake, TX (US); Katie Gralton, Addison, TX (US)

(73) Assignee: MARY KAY INC., Addison, TX (US)

( * ) Notice: Subject to any disclaimer, the term of this patent is extended or adjusted under 35 U.S.C. 154(b) by 0 days.

(21) Appl. No.: 17/452,799

(22) Filed: Oct. 29, 2021

(65) Prior Publication Data

US 2022/0133622 A1 May 5, 2022

Related U.S. Application Data

(60) Provisional application No. 63/108,119, filed on Oct. 30, 2020.

(51) Int. Cl.

| | |
|---|---|
| ***A61K 8/9789*** | (2017.01) |
| ***A61K 8/19*** | (2006.01) |
| ***A61K 8/26*** | (2006.01) |
| ***A61K 8/29*** | (2006.01) |
| ***A61K 8/73*** | (2006.01) |
| ***A61K 8/81*** | (2006.01) |
| ***A61K 8/96*** | (2006.01) |
| ***A61Q 1/10*** | (2006.01) |
| ***A61Q 19/00*** | (2006.01) |
| ***A61Q 19/08*** | (2006.01) |

(52) U.S. Cl.

CPC .............. *A61K 8/9789* (2017.08); *A61K 8/19* (2013.01); *A61K 8/26* (2013.01); *A61K 8/29* (2013.01); *A61K 8/73* (2013.01); *A61K 8/737* (2013.01); *A61K 8/8117* (2013.01); *A61K 8/8188* (2013.01); *A61K 8/965* (2013.01); *A61Q 1/10* (2013.01); *A61Q 19/007* (2013.01); *A61Q 19/08* (2013.01); *A61K 2800/43* (2013.01); *A61K 2800/52* (2013.01); *A61K 2800/56* (2013.01)

(58) Field of Classification Search

CPC .................................................... A61K 8/9789

See application file for complete search history.

(56) References Cited

U.S. PATENT DOCUMENTS

| | | | | |
|---|---|---|---|---|
| 9,770,401 | B2 | 9/2017 | Manning et al. | |
| 10,307,346 | B2 | 6/2019 | Newman et al. | |
| 10,799,435 | B1 * | 10/2020 | Montoya | A61K 8/345 |
| 2004/0141936 | A1 * | 7/2004 | Kropke | A61K 8/8117 424/70.11 |
| 2006/0239950 | A1 * | 10/2006 | Mohammadi | A61K 8/31 424/74 |
| 2016/0089323 | A1 * | 3/2016 | Nijakowski | A61Q 19/00 514/355 |
| 2017/0304658 | A1 * | 10/2017 | Roudot | A61K 8/73 |
| 2018/0256485 | A1 | 9/2018 | Drake | |

FOREIGN PATENT DOCUMENTS

| | | | | |
|---|---|---|---|---|
| BR | 112012031623 | B1 * | 4/2018 | A61K 8/0258 |
| CN | 102406581 | A * | 4/2012 | |
| CN | 104546650 | A * | 4/2015 | |
| CN | 105663018 | | 6/2016 | |
| CN | 109303716 | | 2/2019 | |
| CN | 109310590 | | 2/2019 | |
| EP | 0244859 | | 11/1987 | |
| EP | 0658092 | | 3/1997 | |
| FR | 2902000 | A1 * | 12/2007 | A61K 8/06 |
| KR | 20080041148 | A * | 5/2008 | A61K 8/86 |
| WO | WO 1998/050005 | | 11/1998 | |
| WO | WO-2010105052 | A1 * | 9/2010 | A61P 17/00 |
| WO | WO 2016/090145 | | 6/2016 | |

OTHER PUBLICATIONS

Pharmaceutical and Cosmetic Uses of Fibrous Clays, Developments in Clay Science, 2011 (Year: 2011).*
Ethylhexylglycerin: a low-risk, but highly relevant, sensitizer in "hypo-allergenic" cosmetics, Contact Dermatitis, 2016 (Year: 2016).*
https://b4brands.com/resources/ingredient-directory/isohexadecane/#:~:text=Isohexadecane%20is%20a%20high%20purity,silky%20feeling%20on%20the%20skin. (Year: 2020).*
Translated BR 112012031623 B1 (Year: 2018).*
Translated FR 2902000 A1 (Year: 2007).*
https://incidecoder.com/ingredients/hydroxyethyl-acrylate-sodium-acryloyldimethyl-taurate-copolymer (Year: 2017).*
Wayback Machine (archive.org) for https://incidecoder.com/ingredients/hydroxyethyl-acrylate-sodium-acryloyldimethyl-taurate-copolymer (Year: 2023).*
Amended Safety Assessment of Sodium Sulfate as Used in Cosmetics document (Year: 2016).*
Translated KR 20080041148 A (Year: 2008).*
Translated CN 102406581 A (Year: 2012).*
https://munskin.com/blogs/skin-beauty/vitamin-e#:~:text=The%20four%20tocopherols%E2%80%94alpha%2C%20beta,protect%20itself%20against%20environmental%20pollution. (Year: 2017).*
Wayback for munskin.com (Year: 2023).*
https://www.echemi.com/cms/609857.html#:~:text=Sodium%20Silicate%20has%20been%20used,of%20fine%20lines%20and%20wrinkles. (Year: 2022).*
https://www.cosmeticsinfo.org/ingredient/edta/ (Year: 2013).*
https://blog.essentialwholesale.com/cosmetic-thickeners-and-natural-polymers/#:~:text=Cosmetic%20Thickeners%20and%20Natural%20Polymers,the%20bottom%20of%20this%20post.) (Year: 2023).*

(Continued)

*Primary Examiner* — Andrew S Rosenthal
*Assistant Examiner* — Danielle Kim
(74) *Attorney, Agent, or Firm* — NORTON ROSE FULBRIGHT US LLP

(57) ABSTRACT

The present disclosure provides methods and compositions for treating skin around an eye area of a face. The method entails applying a composition that includes a unique combination of rheology-modifying agents that efficiently maintains active agents in suspension. The composition exhibits pleasing skin feel, softens skin, and attracts and retains moisture while maintaining these desirable properties over time.

17 Claims, 1 Drawing Sheet

(56) References Cited

OTHER PUBLICATIONS https://dopeskin.co/blogs/skincare-ingredient-library/xanthan-gum#:~:text=Again%2C%20this%20helps%20to%20improve,your%20skin%20better%20retain%20moisture.&text=Luckily%2C%20xanthan%20gum%20is%20not,any%20harmful%20side%20effects%20whatsoever. (Year: 2024).*
https://cosmetics.specialchem.com/inci-ingredients/sorbitan-isostearate (Year: 2014).*
Cosmetics Special Chem Mica Date Proof (Year: 2014).*
Cosmetics Info Wayback (Year: 2014).*
Paulas Choice Date Proof (Year: 2020).*
https://foodadditives.net/emulsifiers/polysorbate-60/ (Year: 2020).*
https://shop.skinchakra.eu/en/Cosmetic-Lab/Cosmetic-ingredients-A-Z/Solagum-AX.html (Year: 2020).*
Aerts, Ethylhexylglycerin: a low-risk, but highly relevant, sensitizer in "hypo-allergenic" cosmetics, Contact Dermatitis, 2016 (Year: 2016).*
https://cosmetics.specialchem.com/inci-ingredients/mica (Year: 2014).*
https://www.cosmeticsinfo.org/ingredient/iron-oxides/ (Year: 2014).*
Translated CN 104546650 A (Year: 2015).*
https://www.paulaschoice.com/ingredient-dictionary/ingredient-isohexadecane.html?srsltid=AfmBOoparWI7NzNG3e1UBIPbgloSynVHy1u0qjv2aVgdVQPTIM-m5hcJ (Year: 2020).*
Wayback Machine (archive.org) for https://shop.skinchakra.eu/en/Cosmetic-Lab/Cosmetic-ingredients-A-Z/Solagum-AX.html (Year: 2023).*
Cosmetics Special Chem Sorbitan Isostearate (Year: 2014).*
Amended Safety Assessment of Sodium Sulfate document (Year: 2016).*
Database GNPD [Online] MINTEL; Apr. 2019 (Apr. 2019), "Express Deep Wrinkle Line Filler" Database accession No. 6470219.
Database GNPD [Online] MINTEL; Jun. 2010 (Jun. 2010), "Eye Lift Perfecter" Database accession No. 1357704.
Desplanques et al., "Stabilizing effect of acacia gum on the xanthan helical conformation in aqueous solution" *Food Hydrocolloids* 2014, 35, 181-188.
International Search Report and Written Opinion issued in Corresponding PCT Application No. PCT/US2021/072108, dated Mar. 14, 2022.
*Inspection Technology for Pharmaceutical Excipients and Packaging Materials,* edited by National Institutes for Food and Drug Control, China Medical Science Press, 2019, p. 107 (English Translation of relevant parts provided).
Office Action and Search Report issued in corresponding Chinese Application No. 202111282070.7, dated Mar. 21, 2025 (English translation provided).

* cited by examiner

INSTANT EFFECT EYE CREAM

CROSS-REFERENCE TO RELATED APPLICATIONS

This application claims the benefit of priority to U.S. Provisional Patent Application Ser. No. 63/108,119, filed Oct. 30, 2020, hereby incorporated by reference in its entirety.

BACKGROUND OF THE INVENTION

A. Field of the Invention

The present invention relates generally to a cosmetic skin care composition for improving the appearance of skin under the eyes.

B. Description of Related Art

The skin under the eyes is some of the thinnest, most delicate skin on a person's body. Because of this, the skin under the eyes is one of the first places where visible signs of ageing begin to emerge. As a person ages, the skin loses elasticity and the fat deposits under the eyes start to shrink, which causes a puffy "sunken eye" look. A gradual breakdown of structural proteins leads to "crow's feet," fine lines and wrinkles etched in the skin around the outer corner of the eye.

This area is also more susceptible to environmental influences, including lifestyle choices and external impacts. For example, the skin under the eyes serves as an indicator of a person's lack of sleep. As a person sleeps, skin cells regenerate and produce two vital proteins, collagen and elastin. When a person does not get enough sleep, skin cells have less time to recuperate. This can result in the thin skin under the eyes appearing droopy with dark circles. Taking hot showers can strip the skin in the eye area of essential oils and cause skin dryness. Lack of hydration can also lead to skin dryness, as well as increasing the visibility of the dark capillaries underneath the skin. Stress, fatigue, and even too much salt can lead to swelling or puffiness in the skin around the eyes. Exposure to sunlight, and UV rays in particular, causes breakdown of two structural proteins—collagen and elastin—that the skin needs to stay healthy and youthful. Breakdown of these two crucial proteins leads to looseness in the skin around the eyes.

In order to slow down or reverse damage to skin around the eye, some people make lifestyle alterations, such as getting more sleep or avoiding sunlight. Others resort to eye creams or related personal care compositions for improving the appearance of skin under the eyes.

Two important considerations for personal care compositions are the feel of the composition on the skin and the composition stability. In general, pseudoplastic character and thixotropy are desirable attributes for personal care compositions. Pseudoplasticity (shear thinning) and thixotropic rheology of personal care compositions improve the skin feel of these compositions by imparting a light, non-sticky texture.

Cosmetic stability ensures that the product maintains its desired physical qualities, aesthetics, and intended functionality when stored under appropriate conditions. In general, it is difficult to obtain emulsion-based cosmetic compositions that are stable over time. Upon exposure to increased or decreased temperatures, extremes in pH, or simply over time, one may observe an undesirable change in the texture of a cosmetic composition. This change in texture may be accompanied with drop in viscosity, if it is large enough, may cause phase separation of hydrophobic and hydrophilic components.

SUMMARY OF THE INVENTION

The inventors have developed a composition and method for improving the appearance of skin under the eyes that exhibits good skin feel and maintains its pleasing texture over time. The composition reduces puffiness, exhibits pleasing skin feel, softens skin, and attracts and retains moisture while maintaining these desirable properties over time. The method entails applying the composition to the skin underneath an eye area of a face. The inventors have also developed a method of stabilizing a skin care composition that extends the amount of time over which the composition maintains its initial rheological properties. The stabilizing method entails adding a unique combination of rheology-modifying agents to a skin care composition.

Some aspects of the disclosure are directed to a method of stabilizing a skin care composition comprising adding attapulgite clay, hydroxyethyl acrylate/sodium acryloyldimethyl taurate copolymer, and *Acacia senegal* gum-encapsulated xanthan gum to the skin care composition to form a stabilized skin care composition. In some aspects, the composition comprises from about 0.01 to 10% by weight of attapulgite clay, from about 0.001 to 1% by weight of hydroxyethyl acrylate/sodium acryloyldimethyl taurate copolymer, and from about 0.05 to 5% by weight of *Acacia senegal* gum-encapsulated xanthan gum. In some aspects, the composition comprises from about 0.1 to 5% by weight of attapulgite clay, from about 0.01 to 0.1% by weight of hydroxyethyl acrylate/sodium acryloyldimethyl taurate copolymer, and from about 0.1 to 1% by weight of *Acacia senegal* gum-encapsulated xanthan gum.

In some aspects, the method further comprises adding magnesium aluminum silicate, sodium polystyrene sulfonate, and xanthan gum to the skin care composition. In some aspects, the composition comprises from about 0.2 to 20% by weight of magnesium aluminum silicate, from about 0.1 to 10% by weight of sodium polystyrene sulfonate, and from about 0.02 to 2% by weight of xanthan gum. In some aspects, the composition comprises 2.5 to 7.5% by weight of magnesium aluminum silicate, from about 0.5 to 5% by weight of sodium polystyrene sulfonate, and from about 0.1 to 1% by weight of xanthan gum.

In some aspects, the method further comprises adding one or more of sodium silicate, an alkyl glycol, carrageenan, mica, titanium dioxide, iron oxides, EDTA, ethylhexylglycerin, phenoxyethanol, tocopherol, isohexadecane, polysorbate 60, sodium sulfate, *Cyamopsis tetragonoloba* (guar) gum, and sorbitan isostearate to the skin care composition. In some aspects, the composition comprises from about 0.1 to 10% by weight of sodium silicate, from about 1.5 to 2.5% by weight of alkyl glycol, from about 0.02 to 2% by weight of carrageenan, from about 0.01 to 1% by weight of mica, from about 0.01 to 1% by weight of titanium dioxide, from about 0.01 to 1% by weight of iron oxides, from about 0.01 to 1% by weight of EDTA, from about 0.01 to 1% by weight of ethylhexylglycerin, from about 0.05 to 5% by weight of phenoxyethanol, from about 0.000001 to 0.0001% by weight of tocopherol, from about 0.001 to 1% by weight of isohexadecane, from about 0.001 to 1% by weight of polysorbate 60, from about 0.01 to 1% by weight of sodium sulfate, from about 0.01 to 1% by weight of *Cyamopsis tetragonoloba* (guar) gum, and from about 0.0001 to 0.01% by weight of sorbitan isostearate. In some aspects, the alkyl glycol is selected from the group consisting of ethylene glycol, propylene glycol, butylene glycol, hexylene glycol, ethoxydiglycol, dipropylene glycol, and 1,3-propane diol.

In some aspects, the stabilized skin care composition is stable after one or more freeze and thaw cycles. In some aspects, the stabilized skin care composition is stable after 2, 3, 4, 5, 6, 7, 8, 9, or 10 cycles of freezing the skin care composition then thawing the skin care composition. In some aspects, the stabilized skin care composition has a pH of 10 or greater. In some aspects, an intermediate formulation comprising the attapulgite clay, hydroxyethyl acrylate/sodium acryloyldimethyl taurate copolymer, and *Acacia senegal* gum-encapsulated xanthan gum used to form the stabilized skin care composition has a pH of 10 or greater. In some aspects, stabilizing the skin care composition extends the time over which the skin care composition retains its initial rheological properties. In some aspects, stabilizing the skin care composition increases the temperature range over which the skin care composition is stable. In some aspects, stabilizing the skin care composition increases the temperature range over which the skin care composition is stable. In some aspects, increasing the temperature range over which the skin care composition is stable comprises increasing the maximum temperature of stability and/or decreasing the minimum temperature of stability.

Some aspects of the disclosure are directed to a composition comprising from about 0.01 to 10% by weight of attapulgite clay, from about 0.001 to 1% by weight of hydroxyethyl acrylate/sodium acryloyldimethyl taurate copolymer, and from about 0.05 to 5% by weight of *Acacia senegal* gum-encapsulated xanthan gum. In some aspects, the composition comprises from about 0.1 to 5% by weight of attapulgite clay, from about 0.01 to 0.1% by weight of hydroxyethyl acrylate/sodium acryloyldimethyl taurate copolymer, and from about 0.1 to 1% by weight of *Acacia senegal* gum-encapsulated xanthan gum.

In some aspects, the composition further comprises magnesium aluminum silicate, sodium polystyrene sulfonate, and xanthan gum. In some aspects, the composition further comprises from about 0.2 to 20% by weight of magnesium aluminum silicate, from about 0.1 to 10% by weight of sodium polystyrene sulfonate, and from about 0.02 to 2% by weight of xanthan gum. In some aspects, the composition further comprises from about 2.5 to 7.5% by weight of magnesium aluminum silicate, from about 0.5 to 5% by weight of sodium polystyrene sulfonate, and from about 0.1 to 1% by weight of xanthan gum.

In some aspects, the composition further comprises sodium silicate, an alkyl glycol, carrageenan, mica, titanium dioxide, iron oxides, EDTA, ethylhexylglycerin, phenoxyethanol, tocopherol, isohexadecane, polysorbate 60, sodium sulfate, *Cyamopsis tetragonoloba* (guar) gum, and sorbitan isostearate. In some aspects, the composition further comprises from about 0.1 to 10% by weight of sodium silicate, from about 1.5 to 2.5% by weight of alkyl glycol, from about 0.02 to 2% by weight of carrageenan, from about 0.01 to 1% by weight of mica, from about 0.01 to 1% by weight of titanium dioxide, from about 0.01 to 1% by weight of iron oxides, from about 0.01 to 1% by weight of EDTA, from about 0.01 to 1% by weight of ethylhexylglycerin, from about 0.05 to 5% by weight of phenoxyethanol, from about 0.000001 to 0.0001% by weight of tocopherol, from about 0.001 to 1% by weight of isohexadecane, from about 0.001 to 1% by weight of polysorbate 60, from about 0.01 to 1% by weight of sodium sulfate, from about 0.01 to 1% by weight of *Cyamopsis tetragonoloba* (guar) gum, and from about 0.0001 to 0.01% by weight of sorbitan isostearate. In some aspects, the alkyl glycol is selected from the group consisting of ethylene glycol, propylene glycol, butylene glycol, hexylene glycol, ethoxydiglycol, dipropylene glycol, and 1,3-propane diol.

In some aspects, the composition is provided in the form of an aqueous suspension or a paste. In some aspects, the aqueous suspension in an aqueous mineral suspension. In some aspects, the composition comprises from 60 to 95% by weight of water. In some aspects, the composition is a stabilized skin care composition.

Some aspects of the disclosure are directed to a method of treating skin around an eye area of a face comprising the step of topically applying a composition comprising sodium silicate, sodium polystyrene sulfonate, carrageenan, *Acacia senegal* gum-encapsulated xanthan gum, xanthan gum, and *Cyamopsis tetragonoloba* (guar) gum around the eye area of a face. In some aspects, the composition comprises from about 0.1 to 10% by weight of sodium silicate, from about 0.1 to 10% by weight of sodium polystyrene sulfonate, from about 0.02 to 2% by weight of carrageenan, from about 0.05 to 5% by weight of *Acacia senegal* gum-encapsulated xanthan gum, from about 0.02 to 2% by weight of xanthan gum, and from about 0.01 to 1% by weight of *Cyamopsis tetragonoloba* (guar) gum. In some aspects, treating skin around an eye area of a face reduces puffiness and/or improves skin feel, softens skin, and/or attracts and retains moisture. In some aspects, the composition is applied directly to the skin underneath and laterally outward of a lateral canthal region of an eye area of a face.

In some aspects, the composition of the method further comprises: attapulgite clay and hydroxyethyl acrylate/sodium acryloyldimethyl taurate copolymer; and/or magnesium aluminum silicate. In some aspects, the composition comprises: from about 0.01 to 10% by weight of attapulgite clay and from about 0.001 to 1% by weight of hydroxyethyl acrylate/sodium acryloyldimethyl taurate copolymer; and/or from about 0.2 to 20% by weight of magnesium aluminum silicate. In some aspects, the composition comprises: from about 0.1 to 5% by weight of attapulgite clay and from about 0.01 to 0.1% by weight of hydroxyethyl acrylate/sodium acryloyldimethyl taurate copolymer; and/or from about 2.5 to 7.5% by weight of magnesium aluminum silicate.

In some aspects, the composition of the method further comprises one or more of: an alkyl glycol, mica, titanium dioxide, iron oxides, EDTA, ethylhexylglycerin, phenoxyethanol, tocopherol, isohexadecane, polysorbate 60, and sorbitan isostearate. In some aspects, the composition comprises from about 1.5 to 2.5% by weight of alkyl glycol, from about 0.01 to 1% by weight of mica, from about 0.01 to 1% by weight of titanium dioxide, from about 0.01 to 1% by weight of iron oxides, from about 0.01 to 1% by weight of EDTA, from about 0.01 to 1% by weight of ethylhexylglycerin, from about 0.05 to 5% by weight of phenoxyethanol, from about 0.000001 to 0.0001% by weight of tocopherol, from about 0.001 to 1% by weight of isohexadecane, from about 0.001 to 1% by weight of polysorbate 60, and from about 0.0001 to 0.01% by weight of sorbitan isostearate. In some aspects, the alkyl glycol is selected from the group consisting of ethylene glycol, propylene glycol, butylene glycol, hexylene glycol, ethoxydiglycol, dipropylene glycol, and 1,3-propane diol.

In some aspects, the composition of the method is provided in the form of an aqueous suspension or a paste. In some aspects, the aqueous suspension in an aqueous mineral suspension. In some aspects, the composition comprises from 60 to 95% by weight of water. In some aspects, the composition is a stabilized skin care composition.

Some aspects of the disclosure are directed to a cosmetic composition for the treatment of the skin around the eye of a human comprising from about 0.1 to 10% by weight of sodium silicate, from about 0.1 to 10% by weight of sodium polystyrene sulfonate, from about 0.02 to 2% by weight of carrageenan, from about 0.05 to 5% by weight of *Acacia senegal* gum-encapsulated xanthan gum, from about 0.02 to 2% by weight of xanthan gum, and from about 0.01 to 1% by weight of *Cyamopsis tetragonoloba* (guar) gum.

In some aspects, the composition further comprises: attapulgite clay and hydroxyethyl acrylate/sodium acryloyldimethyl taurate copolymer; and/or magnesium aluminum silicate. In some aspects, the composition further comprises: from about 0.01 to 10% by weight of attapulgite clay and from about 0.001 to 1% by weight of hydroxyethyl acrylate/sodium acryloyldimethyl taurate copolymer; and/or from about 0.2 to 20% by weight of magnesium aluminum silicate. In some aspects, the composition further comprises: from about 0.1 to 5% by weight of attapulgite clay and from about 0.01 to 0.1% by weight of hydroxyethyl acrylate/sodium acryloyldimethyl taurate copolymer; and/or from about 2.5 to 7.5% by weight of magnesium aluminum silicate.

In some aspects, the composition further comprises an alkyl glycol, mica, titanium dioxide, iron oxides, EDTA, ethylhexylglycerin, phenoxyethanol, tocopherol, isohexadecane, polysorbate 60, and sorbitan isostearate. In some aspects, the composition further comprises from about 1.5 to 2.5% by weight of alkyl glycol, from about 0.01 to 1% by weight of mica, from about 0.01 to 1% by weight of titanium dioxide, from about 0.01 to 1% by weight of iron oxides, from about 0.01 to 1% by weight of EDTA, from about 0.01 to 1% by weight of ethylhexylglycerin, from about 0.05 to 5% by weight of phenoxyethanol, from about 0.000001 to 0.0001% by weight of tocopherol, from about 0.001 to 1% by weight of isohexadecane, from about 0.001 to 1% by weight of polysorbate 60, and from about 0.0001 to 0.01% by weight of sorbitan isostearate. In some aspects, the alkyl glycol is selected from the group consisting of ethylene glycol, propylene glycol, butylene glycol, hexylene glycol, ethoxydiglycol, dipropylene glycol, and 1,3-propane diol.

Some aspects of the disclosure are directed to a method of treating skin around an eye area of a face comprising the step of topically applying a cosmetic composition around the eye area of a face. In some aspects, the cosmetic composition is applied directly to the skin underneath and laterally outward of a lateral canthal region of an eye area of a face. In some aspects, treating skin around an eye area of a face reduces puffiness. In some aspects, treating skin around an eye area of a face improves skin feel, softens skin, and attracts and retains moisture.

In some aspects, the cosmetic composition comprises attapulgite clay, polyurethane-39, and *Acacia senegal* gum-encapsulated xanthan gum. In some aspects, the cosmetic composition comprises from about 0.2 to 20% by weight of attapulgite clay, from about 0.05 to 5% by weight of polyurethane-39, and from about 0.05 to 5% by weight of *Acacia senegal* gum-encapsulated xanthan gum. In some aspects, the composition further comprises from about 0.2 to 20% by weight of magnesium aluminum silicate, from about 0.2 to 20% by weight of sodium polystyrene sulfonate and from about 0.02 to 2% by weight of xanthan gum. It was surprisingly found that the combination of attapulgite clay, polyurethane-39, and *Acacia* gum-encapsulated xanthan gum in a topical formulation has increased stability, such as at high pH and during freeze/thaw cycles, when compared to formulations using magnesium aluminum silicate instead of the combination of attapulgite clay, polyurethane-39, and *Acacia* gum-encapsulated xanthan gum.

In some aspects, the composition is provided in the form of an aqueous suspension. In some aspects, the composition is provided in the form of a paste. In some aspects, the composition comprises from 60 to 95% by weight of water. In some aspects, the composition further comprises sodium silicate. In some aspects, the sodium silicate is provided in an amount ranging from 0.1 to 10% by weight.

In some aspects, the composition further comprises one or more of an alkyl glycol, carrageenan, mica, titanium dioxide, EDTA, iron oxides, ethylhexylglycerin, phenoxyethanol, tocopherol, polyisobutene, and polyacrylate-13. In some aspects, the alkyl glycol is selected from the group consisting of ethylene glycol, propylene glycol, butylene glycol, hexylene glycol, ethoxydiglycol, dipropylene glycol, and 1,3-propane diol. In some aspects, the composition comprises 1.5 to 2.5% by weight of alkyl glycol. In some aspects, the composition comprises from about 0.05 to 5% by weight of phenoxyethanol, from about 0.01 to 1% by weight of ethylhexylglycerin, from about 0.02 to 2% by weight of carrageenan, and from about 0.01 to 1% by weight of EDTA. In some aspects, the composition comprises from about 0.02 to 2% by weight of polyisobutene and from about 0.02 to 2% by weight of polyacrylate-13. In some aspects, the composition further comprises from about 0.01 to 1% by weight of mica, from about 0.01 to 1% by weight of titanium dioxide, and from about 0.01 to 1% by weight of iron oxides.

In some aspects, the composition comprises from about 2.5 to 7.5% by weight of attapulgite clay. In some aspects, the composition comprises from about 0.1 to 1% by weight of *Acacia senegal* gum-encapsulated xanthan gum. In some aspects, the composition comprises 1 to 2.5% by weight of polyurethane-39. In some aspects, the composition comprises 2.5 to 7.5% by weight of sodium polystyrene sulfonate. In some aspects, the composition comprises 2.5 to 7.5% by weight of magnesium aluminum silicate. In some aspects, the composition comprises from about 0.1 to 1% by weight of xanthan gum. In some aspects, a cosmetic composition comprising attapulgite clay, polyurethane-39, and *Acacia senegal* gum-encapsulated xanthan gum is a stabilized skin care composition.

Some aspects of the disclosure are directed to a cosmetic composition for the treatment of the skin around the eye of a human comprising from about 0.2 to 20% by weight of magnesium aluminum silicate, from about 0.2 to 20% by weight of sodium polystyrene sulfonate, and from about 0.02 to 2% by weight of xanthan gum. In some aspects, the composition is provided in the form of an aqueous suspension. In some aspects, the composition is provided in the form of a paste. In some aspects, the composition comprises from 60 to 95% by weight of water. In some aspects, the composition further comprises sodium silicate. In some aspects, the sodium silicate is provided in an amount ranging from 0.1 to 10% by weight. In some aspects, the composition further comprises one or more of an alkyl glycol, carrageenan, mica, titanium dioxide, EDTA, iron oxides, ethylhexylglycerin, phenoxyethanol, tocopherol, polyisobutene, and polyacrylate-13. In some aspects, the alkyl glycol is selected from the group consisting of ethylene glycol, propylene glycol, butylene glycol, hexylene glycol, ethoxydiglycol, dipropylene glycol, and 1,3-propane diol. In some aspects, the composition comprises 1.5 to 2.5% by weight of alkyl glycol. In some aspects, the composition comprises from about 0.05 to 5% by weight of phenoxyethanol, from about 0.01 to 1% by weight of ethylhexylglycerin, from about 0.02 to 2% by weight of carrageenan, and from about 0.01 to 1% by weight of EDTA. In some aspects, the composition comprises from about 0.02 to 2% by weight of polyisobutene and from about 0.02 to 2% by weight of polyacrylate-13. In some aspects, the composition further comprises from about 0.01 to 1% by weight of mica, from about 0.01 to 1% by weight of titanium dioxide, and from about 0.01 to 1% by weight of iron oxides. In some aspects, the composition comprises from about 2.5 to 7.5% by weight of magnesium aluminum silicate. In some aspects, the composition comprises from about 2.5 to 7.5% of sodium polystyrene sulfonate. In some aspects, the composition comprises from about 0.1 to 1% by weight of xanthan gum. In some aspects, the composition further comprises attapulgite clay, polyurethane-39, and *Acacia senegal* gum-encapsulated xanthan gum. In some aspects, the composition comprises from about 0.2 to 20% by weight of attapulgite clay, from about 0.05 to 5% by weight of polyurethane-39, and from about 0.05 to 5% by weight of *Acacia senegal* gum-encapsulated xanthan gum.

Some aspects of the disclosure are directed to improving a condition or appearance of skin, comprising applying any one of the compositions disclosed herein to skin in need thereof. In some aspects, any one of the compositions disclosed herein is applied to skin and the composition is left on the skin, or alternatively removed from the skin after a period of time. In some aspects, the composition is applied directly to a subject's skin around the eye area. In some aspects, the compositions disclosed herein are used to reduce puffiness. In some aspects, the compositions disclosed herein are used to improve skin feel, soften skin, and attract and retain moisture.

Some aspects of the disclosure are directed to a method of stabilizing a skin care composition. In some aspects, a method of stabilizing a skin care composition comprises adding attapulgite clay, polyurethane-39, and *Acacia senegal* gum-encapsulated xanthan gum to a skin care composition to form a stabilized skin care composition. In some aspects, the method of stabilizing a skin care composition comprises adding from about 0.2 to 20% by weight of attapulgite clay, from about 0.05 to 5% by weight of polyurethane-39, and from about 0.05 to 5% by weight of *Acacia senegal* gum-encapsulated xanthan gum to the skin care composition to form a stabilized skin care composition. In some aspects, stabilizing a skin care composition extends the time over which the composition retains its initial rheological properties. In some aspects, stabilizing a skin care composition allows the composition to retain its stability through one or more freeze-thaw cycles. In some aspects, stabilizing a skin care composition allows the composition to retain its rheological properties through one or more freeze-thaw cycles. In some aspects, multiple freeze-thaw cycles involves 2, 3, 4, 5, 6, 7, 8, 9, or 10 cycles of freezing the composition then thawing the composition. In some aspects, the stabilized skin care composition has a pH of 10 or greater. In some aspects, an intermediate formulation comprising the attapulgite clay, polyurethane-39, and *Acacia senegal* gum-encapsulated xanthan gum that is used to form the stabilized skin care composition has a pH of 10 or greater. In some aspects, the method of stabilizing a skin care composition increases the temperature range over which the composition is stable. Increasing the temperature range over which the composition is stable may include increasing the maximum temperature of stability, decreasing the minimum temperature of stability, or both.

In some aspects, the compositions of the present invention are formulated as a topical skin composition. In some aspects, the composition is in the form of an aqueous suspension. In some aspects, the aqueous suspension is a mineral suspension. In some aspects, the composition is in the form of a paste. The composition can be formulated for topical skin application at least 1, 2, 3, 4, 5, 6, 7, or more times a day during use. In some aspects of the present invention, compositions can be storage stable. It is also contemplated that the degree of dissolution of the composition can be selected to achieve a desired result, e.g., depending on the type of composition desired. In some aspects, the composition is applied directly to the skin. In some aspects, the composition is added to a subject's current skin care product. The resulting combination of the composition interspersed within the subject's skin care product may then be applied directly to the user's skin.

The compositions in non-limiting aspects can be formulated to provide a pH of about 6 to about 9. In some aspects, the pH is 10 or greater. In some aspects, the pH can be 1, 2, 3, 4, 5, 6, 7, 8, 9, 10, 11, 12, 13, or 14. The compositions can include a mono-, di-, or tri-glyceride. Non-limiting examples include small, medium, and large chain mono-, di-, or tri-glycerides. In some aspects, an exemplary triglyceride is a medium chain triglyceride (e.g., caprylic capric triglyceride). The compositions can also include preservatives. Non-limiting examples of preservatives include methylparaben, propylparaben, or a mixture of methylparaben and propylparaben. In some aspects, the composition is paraben-free. Polyacrylate-13 is a copolymer of acrylate (or acrylic acid), acrylamide, and acryloyldimethyl taurate.

The composition may be provided in a packaging that dispenses a pre-measured amount of the composition. The compositions of the present disclosure can also include any one of, any combination of, or all of the following additional ingredients: water, a conditioning agent, moisturizing agent, structuring agent, emollient, tackifier, plasticizer, surfactant, emulsifier, colorant, preservative, pH adjustor, reducing agent, fragrance, foaming agent, tanning agent, astringent, antiseptic, deodorant, antiperspirant, lightener, adhesive, UV absorption agent, UV reflection agent, a thickening agent, exfoliating agent, a silicone containing compound, an essential oil, a vitamin, a pharmaceutical ingredient, an antioxidant, biocide, or any combination of such ingredients or mixtures of such ingredients. In certain aspects, the composition can include at least two, three, four, five, six, seven, eight, nine, ten, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

It is also contemplated that the compositions disclosed throughout this specification can be used as a leave-on or rinse-off composition. By way of example, a leave-on composition can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or overnight or throughout the day). Alternatively, a rinse-off composition can be a product that is intended to be applied to the skin and then removed or rinsed from the skin (e.g., with water) within a period of time such as less than 5, 4, 3, 2, or 1 minute.

In some instances, a second skin care composition is applied to the skin before application of the composition to the skin. In some instances, more than one skin care composition is applied to the skin before application of the composition to the skin. In some instances, the composition is combined with a third skin care composition prior to application to the skin. In some instances, the third skin care composition affects a condition or appearance of the skin. In some instances, the third skin care composition does not affect a condition or appearance of the skin.

It is contemplated that any embodiment discussed in this specification can be implemented with respect to any method or composition of the invention, and vice versa. Furthermore, compositions of the invention can be used to achieve methods of the invention.

In one embodiment, the compositions of the present invention can be pharmaceutically or cosmetically elegant or can have pleasant tactile properties. "Pharmaceutically elegant," "cosmetically elegant," and/or "pleasant tactile properties" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

Also disclosed are the following Embodiments 1 to 102 of the present disclosure. Embodiment 1 is a method of stabilizing a skin care composition comprising adding attapulgite clay, hydroxyethyl acrylate/sodium acryloyldimethyl taurate copolymer, and *Acacia senegal* gum-encapsulated xanthan gum to the skin care composition to form a stabilized skin care composition. Embodiment 2 is the method of embodiment 1, wherein the composition comprises from about 0.01 to 10% by weight of attapulgite clay, from about 0.001 to 1% by weight of hydroxyethyl acrylate/sodium acryloyldimethyl taurate copolymer, and from about 0.05 to 5% by weight of *Acacia senegal* gum-encapsulated xanthan gum. Embodiment 3 is the method of Embodiments 1 to 2, wherein the composition comprises from about 0.1 to 5% by weight of attapulgite clay, from about 0.01 to 0.1% by weight of hydroxyethyl acrylate/sodium acryloyldimethyl taurate copolymer, and from about 0.1 to 1% by weight of *Acacia senegal* gum-encapsulated xanthan gum. Embodiment 4 is the method of Embodiments 1 to 3, wherein the method further comprises adding magnesium aluminum silicate, sodium polystyrene sulfonate, and xanthan gum to the skin care composition. Embodiment 5 is the method of Embodiments 1 to 4, wherein the method further comprises adding magnesium aluminum silicate, sodium polystyrene sulfonate, and xanthan gum to the skin care composition, and wherein the composition comprises from about 0.2 to 20% by weight of magnesium aluminum silicate, from about 0.1 to 10% by weight of sodium polystyrene sulfonate, and from about 0.02 to 2% by weight of xanthan gum. Embodiment 6 is the method of Embodiments 1 to 5, wherein the method further comprises adding magnesium aluminum silicate, sodium polystyrene sulfonate, and xanthan gum to the skin care composition, and wherein the composition comprises 2.5 to 7.5% by weight of magnesium aluminum silicate, from about 0.5 to 5% by weight of sodium polystyrene sulfonate, and from about 0.1 to 1% by weight of xanthan gum. Embodiment 7 is the method of Embodiments 1 to 6, wherein the method further comprises adding one or more of sodium silicate, an alkyl glycol, carrageenan, mica, titanium dioxide, iron oxides, EDTA, ethylhexylglycerin, phenoxyethanol, tocopherol, sodium sulfate, *Cyamopsis tetragonoloba* (guar) gum, isohexadecane, polysorbate 60, and sorbitan isostearate to the skin care composition. Embodiment 8 is the method of Embodiments 1 to 7, wherein the method further comprises adding one or more of sodium silicate, an alkyl glycol, carrageenan, mica, titanium dioxide, iron oxides, EDTA, ethylhexylglycerin, phenoxyethanol, tocopherol, isohexadecane, polysorbate 60, sodium sulfate, *Cyamopsis tetragonoloba* (guar) gum, and sorbitan isostearate to the skin care composition, and wherein the composition comprises from about 0.1 to 10% by weight of sodium silicate, from about 1.5 to 2.5% by weight of alkyl glycol, from about 0.02 to 2% by weight of carrageenan, from about 0.01 to 1% by weight of mica, from about 0.01 to 1% by weight of titanium dioxide, from about 0.01 to 1% by weight of iron oxides, from about 0.01 to 1% by weight of EDTA, from about 0.01 to 1% by weight of ethylhexylglycerin, from about 0.05 to 5% by weight of phenoxyethanol, from about 0.000001 to 0.0001% by weight of tocopherol, from about 0.001 to 1% by weight of isohexadecane, from about 0.001 to 1% by weight of polysorbate 60, from about 0.01 to 1% by weight of sodium sulfate, from about 0.01 to 1% by weight of *Cyamopsis tetragonoloba* (guar) gum, and from about 0.0001 to 0.01% by weight of sorbitan isostearate. Embodiment 9 is the method of Embodiments 1 to 8, wherein the method further comprises adding one or more of sodium silicate, an alkyl glycol, carrageenan, mica, titanium dioxide, iron oxides, EDTA, ethylhexylglycerin, phenoxyethanol, tocopherol, isohexadecane, polysorbate 60, sodium sulfate, *Cyamopsis tetragonoloba* (guar) gum, and sorbitan isostearate to the skin care composition, and wherein the alkyl glycol is selected from the group consisting of ethylene glycol, propylene glycol, butylene glycol, hexylene glycol, ethoxydiglycol, dipropylene glycol, and 1,3-propane diol. Embodiment 10 is the method of Embodiments 1 to 9, wherein the stabilized skin care composition is stable after one or more freeze and thaw cycles. Embodiment 11 is the method of Embodiments 1 to 10, wherein the stabilized skin care composition is stable after 2, 3, 4, 5, 6, 7, 8, 9, or 10 cycles of freezing the skin care composition then thawing the skin care composition. Embodiment 12 is the method of Embodiments 1 to 11, wherein the stabilized skin care composition has a pH of 10 or greater. Embodiment 13 is the method of Embodiments 1 to 12, wherein an intermediate formulation comprising the attapulgite clay, hydroxyethyl acrylate/sodium acryloyldimethyl taurate copolymer, and *Acacia senegal* gum-encapsulated xanthan gum used to form the stabilized skin care composition has a pH of 10 or greater. Embodiment 14 is the method of Embodiments 1 to 13, wherein stabilizing the skin care composition extends the time over which the skin care composition retains its initial rheological properties. Embodiment 15 is the method of Embodiments 1 to 14, wherein stabilizing the skin care composition increases the temperature range over which the skin care composition is stable. Embodiment 16 is the method of Embodiments 1 to 15, wherein stabilizing the skin care composition increases the temperature range over which the skin care composition is stable, and wherein increasing the temperature range over which the skin care composition is stable comprises increasing the maximum temperature of stability and/or decreasing the minimum temperature of stability.

Embodiment 17 is a composition comprising attapulgite clay, hydroxyethyl acrylate/sodium acryloyldimethyl taurate copolymer, and *Acacia senegal* gum-encapsulated xanthan gum to the skin care composition to form a stabilized skin care composition. Embodiment 18 is the composition of Embodiment 17, wherein the composition comprises from about 0.01 to 10% by weight of attapulgite clay, from about 0.001 to 1% by weight of hydroxyethyl acrylate/sodium acryloyldimethyl taurate copolymer, and from about 0.05 to 5% by weight of *Acacia senegal* gum-encapsulated xanthan gum. Embodiment 19 is the composition of Embodiments 17 to 18, wherein the composition comprises from about 0.1 to 5% by weight of attapulgite clay, from about 0.01 to 0.1% by weight of hydroxyethyl acrylate/sodium acryloyldimethyl taurate copolymer, and from about 0.1 to 1% by weight of *Acacia senegal* gum-encapsulated xanthan gum. Embodiment 20 is the composition of Embodiments 17 to 19, wherein the composition further comprises magnesium aluminum silicate, sodium polystyrene sulfonate, and xanthan gum. Embodiment 21 is the composition of Embodiments 17 to 20, wherein the composition further comprises magnesium aluminum silicate, sodium polystyrene sulfonate, and xanthan gum, and wherein the composition comprises from about 0.2 to 20% by weight of magnesium aluminum silicate, from about 0.1 to 10% by weight of sodium polystyrene sulfonate, and from about 0.02 to 2% by weight of xanthan gum. Embodiment 22 is the composition of Embodiments 17 to 21, wherein the composition further comprises magnesium aluminum silicate, sodium polystyrene sulfonate, and xanthan gum, and wherein the composition comprises 2.5 to 7.5% by weight of magnesium aluminum silicate, from about 0.5 to 5% by weight of sodium polystyrene sulfonate, and from about 0.1 to 1% by weight of xanthan gum. Embodiment 23 is the composition of Embodiments 17 to 22, wherein the composition further comprises one or more of sodium silicate, an alkyl glycol, carrageenan, mica, titanium dioxide, iron oxides, EDTA, ethylhexylglycerin, phenoxyethanol, tocopherol, isohexadecane, polysorbate 60, sodium sulfate, *Cyamopsis tetragonoloba* (guar) gum, and sorbitan isostearate. Embodiment 24 is the composition of Embodiments 17 to 25, wherein the composition further comprises one or more of sodium silicate, an alkyl glycol, carrageenan, mica, titanium dioxide, iron oxides, EDTA, ethylhexylglycerin, phenoxyethanol, tocopherol, isohexadecane, polysorbate 60, sodium sulfate, *Cyamopsis tetragonoloba* (guar) gum, and sorbitan isostearate, and wherein the composition comprises from about 0.1 to 10% by weight of sodium silicate, from about 1.5 to 2.5% by weight of alkyl glycol, from about 0.02 to 2% by weight of carrageenan, from about 0.01 to 1% by weight of mica, from about 0.01 to 1% by weight of titanium dioxide, from about 0.01 to 1% by weight of iron oxides, from about 0.01 to 1% by weight of EDTA, from about 0.01 to 1% by weight of ethylhexylglycerin, from about 0.05 to 5% by weight of phenoxyethanol, from about 0.000001 to 0.0001% by weight of tocopherol, from about 0.001 to 1% by weight of isohexadecane, from about 0.001 to 1% by weight of polysorbate 60, from about 0.01 to 1% by weight of sodium sulfate, from about 0.01 to 1% by weight of *Cyamopsis tetragonoloba* (guar) gum, and from about 0.0001 to 0.01% by weight of sorbitan isostearate. Embodiment 25 is the composition of Embodiments 17 to 24, wherein the composition further comprises one or more of sodium silicate, an alkyl glycol, carrageenan, mica, titanium dioxide, iron oxides, EDTA, ethylhexylglycerin, phenoxyethanol, tocopherol, isohexadecane, polysorbate 60, sodium sulfate, *Cyamopsis tetragonoloba* (guar) gum, and sorbitan isostearate, and wherein the alkyl glycol is selected from the group consisting of ethylene glycol, propylene glycol, butylene glycol, hexylene glycol, ethoxydiglycol, dipropylene glycol, and 1,3-propane diol. Embodiment 26 is the composition of Embodiments 17 to 25, wherein the composition is provided in the form of an aqueous suspension or a paste, and wherein the aqueous suspension in an aqueous mineral suspension. Embodiment 27 is the composition of Embodiments 17 to 26, wherein the composition comprises from 60 to 95% by weight of water. Embodiment 28 is the composition of Embodiments 17 to 27, wherein the composition is a stabilized skin care composition.

Embodiment 29 is a method of treating skin around an eye area of a face comprising the step of topically applying a composition comprising sodium silicate, sodium polystyrene sulfonate, carrageenan, *Acacia senegal* gum-encapsulated xanthan gum, xanthan gum, and *Cyamopsis tetragonoloba* (guar) gum around the eye area of a face. Embodiment 30 is the method of Embodiment 29, wherein the composition comprises from about 0.1 to 10% by weight of sodium silicate, from about 0.1 to 10% by weight of sodium polystyrene sulfonate, from about 0.02 to 2% by weight of carrageenan, from about 0.05 to 5% by weight of *Acacia senegal* gum-encapsulated xanthan gum, from about 0.02 to 2% by weight of xanthan gum, and from about 0.01 to 1% by weight of *Cyamopsis tetragonoloba* (guar) gum. Embodiment 31 is the method of Embodiments 29 to 30, wherein the composition further comprises attapulgite clay and hydroxyethyl acrylate/sodium acryloyldimethyl taurate copolymer. Embodiment 32 is the method of Embodiments 29 to 31, wherein the composition further comprises from about 0.01 to 10% by weight of attapulgite clay and from about 0.001 to 1% by weight of hydroxyethyl acrylate/sodium acryloyldimethyl taurate copolymer. Embodiment 33 is the method of Embodiments 29 to 32, wherein the composition further comprises from about 0.1 to 5% by weight of attapulgite clay and from about 0.01 to 0.1% by weight of hydroxyethyl acrylate/sodium acryloyldimethyl taurate copolymer. Embodiment 34 is the method of Embodiments 29 to 33, wherein the composition further comprises magnesium aluminum silicate. Embodiment 35 is the method of Embodiments 29 to 34, wherein the composition further comprises from about 0.2 to 20% by weight of magnesium aluminum silicate. Embodiment 36 is the method of Embodiments 29 to 35, wherein the composition further comprises from about 2.5 to 7.5% by weight of magnesium aluminum silicate. Embodiment 37 is the method of Embodiments 29 to 36, wherein the composition further comprises one or more of: an alkyl glycol, mica, titanium dioxide, iron oxides, EDTA, ethylhexylglycerin, phenoxyethanol, tocopherol, isohexadecane, polysorbate 60, and sorbitan isostearate. Embodiment 38 is the method of Embodiments 29 to 37, wherein the composition further comprises one or more of: an alkyl glycol, mica, titanium dioxide, iron oxides, EDTA, ethylhexylglycerin, phenoxyethanol, tocopherol, isohexadecane, polysorbate 60, and sorbitan isostearate, and wherein the alkyl glycol is selected from the group consisting of ethylene glycol, propylene glycol, butylene glycol, hexylene glycol, ethoxydiglycol, dipropylene glycol, and 1,3-propane diol. Embodiment 39 is the method of Embodiments 29 to 38, wherein the composition further comprises from about from about 1.5 to 2.5% by weight of alkyl glycol, from about 0.01 to 1% by weight of mica, from about 0.01 to 1% by weight of titanium dioxide, from about 0.01 to 1% by weight of iron oxides, from about 0.01 to 1% by weight of EDTA, from about 0.01 to 1% by weight of ethylhexylglycerin, from about 0.05 to 5% by weight of phenoxyethanol, from about 0.000001 to 0.0001% by weight of tocopherol, from about 0.001 to 1% by weight of isohexadecane, from about 0.001 to 1% by weight of polysorbate 60, and from about 0.0001 to 0.01% by weight of sorbitan isostearate. Embodiment 40 is the method of Embodiments 29 to 39, wherein treating skin around an eye area of a face reduces puffiness and/or improves skin feel, softens skin, and/or attracts and retains moisture. Embodiment 41 is the method of Embodiments 29 to 40, wherein the composition is applied directly to the skin underneath and laterally outward of a lateral canthal region of an eye area of a face.

Embodiment 42 is a cosmetic composition for the treatment of the skin around the eye of a human comprising sodium silicate, sodium polystyrene sulfonate, carrageenan, *Acacia senegal* gum-encapsulated xanthan gum, xanthan gum, and *Cyamopsis tetragonoloba* (guar) gum. Embodiment 43 is the cosmetic composition of Embodiment 42, wherein the composition comprises from about 0.1 to 10% by weight of sodium silicate, from about 0.1 to 10% by weight of sodium polystyrene sulfonate, from about 0.02 to 2% by weight of carrageenan, from about 0.05 to 5% by weight of *Acacia senegal* gum-encapsulated xanthan gum, from about 0.02 to 2% by weight of xanthan gum, and from about 0.01 to 1% by weight of *Cyamopsis tetragonoloba* (guar) gum. Embodiment 44 is the cosmetic composition of Embodiments 42 to 43, wherein the composition further comprises attapulgite clay and hydroxyethyl acrylate/sodium acryloyldimethyl taurate copolymer. Embodiment 45 is the cosmetic composition of Embodiments 42 to 44, wherein the composition further comprises from about 0.01 to 10% by weight of attapulgite clay and from about 0.001 to 1% by weight of hydroxyethyl acrylate/sodium acryloyldimethyl taurate copolymer. Embodiment 46 is the composition of Embodiments 42 to 45, wherein the composition further comprises from about 0.1 to 5% by weight of attapulgite clay and from about 0.01 to 0.1% by weight of hydroxyethyl acrylate/sodium acryloyldimethyl taurate copolymer. Embodiment 47 is the composition of Embodiments 42 to 46, wherein the composition further comprises magnesium aluminum silicate. Embodiment 48 is the composition of Embodiments 42 to 47, wherein the composition further comprises from about 0.2 to 20% by weight of magnesium aluminum silicate. Embodiment 49 is the composition of Embodiments 42 to 48, wherein the composition further comprises from about 2.5 to 7.5% by weight of magnesium aluminum silicate. Embodiment 50 is the composition of Embodiments 42 to 49 wherein the composition further comprises an alkyl glycol, mica, titanium dioxide, iron oxides, EDTA, ethylhexylglycerin, phenoxyethanol, tocopherol, isohexadecane, polysorbate 60, and sorbitan isostearate. Embodiment 51 is the composition of Embodiments 42 to 50, wherein the composition further comprises one or more of: an alkyl glycol, mica, titanium dioxide, iron oxides, EDTA, ethylhexylglycerin, phenoxyethanol, tocopherol, isohexadecane, polysorbate 60, and sorbitan isostearate, and wherein the alkyl glycol is selected from the group consisting of ethylene glycol, propylene glycol, butylene glycol, hexylene glycol, ethoxydiglycol, dipropylene glycol, and 1,3-propane diol. Embodiment 52 is the composition of Embodiments 42 to 51, wherein the composition further comprises from about 1.5 to 2.5% by weight of alkyl glycol, from about 0.01 to 1% by weight of mica, from about 0.01 to 1% by weight of titanium dioxide, from about 0.01 to 1% by weight of iron oxides, from about 0.01 to 1% by weight of EDTA, from about 0.01 to 1% by weight of ethylhexylglycerin, from about 0.05 to 5% by weight of phenoxyethanol, from about 0.000001 to 0.0001% by weight of tocopherol, from about 0.001 to 1% by weight of isohexadecane, from about 0.001 to 1% by weight of polysorbate 60, and from about 0.0001 to 0.01% by weight of sorbitan isostearate. Embodiment 53 is the composition of Embodiments 42 to 52, wherein the composition is provided in the form of an aqueous suspension or a paste. Embodiment 54 is the composition of Embodiments 42 to 53, wherein the composition is provided in the form of an aqueous suspension or a paste, and wherein the aqueous suspension in an aqueous mineral suspension. Embodiment 55 is the composition of Embodiments 42 to 54, wherein the composition comprises from 60 to 95% by weight of water. Embodiment 56 is the composition of Embodiments 42 to 55, wherein the composition is a stabilized skin care composition.

Embodiment 57 is a cosmetic composition comprising attapulgite clay, polyurethane-39, and *Acacia senegal* gum-encapsulated xanthan gum. Embodiment 58 is the composition of Embodiment 57, wherein the composition comprises from about 0.2 to 20% by weight of attapulgite clay, from about 0.05 to 5% by weight of polyurethane-39, and from about 0.05 to 5% by weight of *Acacia senegal* gum-encapsulated xanthan gum. Embodiment 59 is the composition of Embodiments 57 to 58, wherein the composition further comprises from about 0.2 to 20% by weight of magnesium aluminum silicate, from about 0.2 to 20% by weight of sodium polystyrene sulfonate, and from about 0.02 to 2% by weight of xanthan gum. Embodiment 60 is the composition of Embodiments 57 to 59, wherein the composition is provided in the form of an aqueous suspension or a paste. Embodiment 61 is the composition of Embodiments 57 to 60, wherein the composition comprises from 60 to 95% by weight of water. Embodiment 62 is the composition of Embodiments 57 to 61, wherein the composition further comprises sodium silicate. Embodiment 63 is the composition of Embodiments 57 to 62, wherein the sodium silicate is provided in an amount ranging from 0.1 to 10% by weight. Embodiment 64 is the composition of Embodiments 57 to 63, wherein the composition further comprises one or more of: an alkyl glycol, carrageenan, mica, titanium dioxide, EDTA, iron oxides, ethylhexylglycerin, phenoxyethanol, tocopherol, polyisobutene, and polyacrylate-13. Embodiment 65 is the composition of Embodiments 57 to 64, wherein the composition further comprises: from about 0.05 to 5% by weight of phenoxyethanol, from about 0.01 to 1% by weight of ethylhexylglycerin, from about 0.02 to 2% by weight of carrageenan, from about 0.02 to 2% by weight of polyisobutene, from about 0.02 to 2% by weight of polyacrylate-13, and from about 0.01 to 1% by weight of EDTA. Embodiment 66 is the composition of Embodiments 57 to 65, wherein the composition further comprises: from about 0.01 to 1% by weight of mica, from about 0.01 to 1% by weight of titanium dioxide, and from about 0.01 to 1% by weight of iron oxides. Embodiment 67 is the composition of Embodiments 57 to 66, wherein the composition comprises from about 2.5 to 7.5% by weight of attapulgite clay. Embodiment 68 is the composition of Embodiments 57 to 67, wherein the composition comprises from about 0.1 to 1% by weight of *Acacia senegal* gum-encapsulated xanthan gum. Embodiment 69 is the composition of Embodiments 57 to 68, wherein the composition comprises 1 to 2.5% by weight of polyurethane-39. Embodiment 70 is the composition of Embodiments 57 to 69, wherein the composition comprises 2.5 to 7.5% by weight of sodium polystyrene sulfonate. Embodiment 71 is the composition of Embodiments 57 to 70, wherein the composition comprises from about 0.1 to 1% by weight of xanthan gum. Embodiment 72 is the composition of Embodiments 57 to 71, wherein the composition comprises from about 2.5 to 7.5% by weight of magnesium aluminum silicate. Embodiment 73 is the composition of Embodiments 57 to 72, wherein the composition further comprises an alkyl glycol, and wherein the alkyl glycol is selected from the group consisting of ethylene glycol, propylene glycol, butylene glycol, hexylene glycol, ethoxydiglycol, dipropylene glycol, and 1,3-propane diol. Embodiment 74 is the composition of Embodiments 57 to 73, wherein the composition further comprises an alkyl glycol, and wherein the composition comprises 1.5 to 2.5% by weight of alkyl glycol.

Embodiment 75 is a cosmetic composition for the treatment of the skin around the eye of a human comprising from about 0.2 to 20% by weight of magnesium aluminum silicate, from about 0.2 to 20% by weight of sodium polystyrene sulfonate, and from about 0.02 to 2% by weight of xanthan gum. Embodiment 76 is composition of Embodiment 75, wherein the composition is provided in the form of an aqueous suspension or a paste. Embodiment 77 is the composition of Embodiments 75 to 76, wherein the composition comprises from 60 to 95% by weight of water. Embodiment 78 is the composition of Embodiments 75 to 77, wherein the composition further comprises sodium silicate. Embodiment 79 is the composition of Embodiments 75 to 78, wherein the composition further comprises sodium silicate, and wherein the sodium silicate is provided in an amount ranging from 0.1 to 10% by weight. Embodiment 80 is the composition of Embodiments 75 to 79, wherein the composition further comprises one or more of: an alkyl glycol, carrageenan, mica, titanium dioxide, EDTA, iron oxides, ethylhexylglycerin, phenoxyethanol, tocopherol, polyisobutene, and polyacrylate-13. Embodiment 81 is the composition of Embodiments 75 to 80, wherein the composition further comprises: from about 0.05 to 5% by weight of phenoxyethanol, from about 0.01 to 1% by weight of ethylhexylglycerin, from about 0.02 to 2% by weight of carrageenan, from about 0.02 to 2% by weight of polyisobutene, from about 0.02 to 2% by weight of polyacrylate-13, and from about 0.01 to 1% by weight of EDTA. Embodiment 82 is the composition of Embodiments 75 to 81, wherein the composition further comprises: from about 0.01 to 1% by weight of mica, from about 0.01 to 1% by weight of titanium dioxide, and from about 0.01 to 1% by weight of iron oxides. Embodiment 83 is the composition of Embodiments 75 to 82, wherein the composition further comprises attapulgite clay, polyurethane-39, and *Acacia senegal* gum-encapsulated xanthan gum. Embodiment 84 is the composition of Embodiments 75 to 83, wherein the composition further comprises attapulgite clay, polyurethane-39, and *Acacia senegal* gum-encapsulated xanthan gum, and wherein the composition comprises from about 0.2 to 20% by weight of attapulgite clay, from about 0.05 to 5% by weight of polyurethane-39, and from about 0.05 to 5% by weight of *Acacia senegal* gum-encapsulated xanthan gum. Embodiment 85 is the composition of Embodiments 75 to 84, wherein the composition comprises 2.5 to 7.5% by weight of magnesium aluminum silicate. Embodiment 86 is the composition of Embodiments 75 to 85 wherein the composition comprises 2.5 to 7.5% by weight of sodium polystyrene sulfonate. Embodiment 87 is the composition of Embodiments 75 to 86, wherein the composition comprises from about 0.1 to 1% by weight of xanthan gum. Embodiment 88 is the composition of Embodiments 75 to 87, wherein the composition further comprises an alkyl glycol, and wherein the alkyl glycol is selected from the group consisting of ethylene glycol, propylene glycol, butylene glycol, hexylene glycol, ethoxydiglycol, dipropylene glycol, and 1,3-propane diol. Embodiment 89 is the composition of Embodiments 75 to 88, wherein the composition further comprises an alkyl glycol, and wherein the composition comprises 1.5 to 2.5% by weight of alkyl glycol.

Embodiment 90 is a method of treating skin around an eye area of a face comprising the step of topically applying the composition of any one of Embodiments 57 to 74 or 75 to 89 around the eye area of a face. Embodiment 91 is the method of Embodiment 90, wherein treating skin around an eye area of a face reduces puffiness. Embodiment 92 is the method of Embodiments 90 to 91, wherein treating skin around an eye area of a face improves skin feel, softens skin, and attracts and retains moisture. Embodiment 93 is the method of Embodiments 90 to 92, wherein the composition is applied directly to the skin underneath and laterally outward of a lateral canthal region of an eye area of a face.

Embodiment 94 is a method of stabilizing a skin care composition comprising adding attapulgite clay, polyurethane-39, and *Acacia senegal* gum-encapsulated xanthan gum to a skin care composition to form a stabilized skin care composition. Embodiment 85 is the method of Embodiment 94, wherein the method comprises adding from about 0.2 to 20% by weight of attapulgite clay, from about 0.05 to 5% by weight of polyurethane-39, and from about 0.05 to 5% by weight of *Acacia senegal* gum-encapsulated xanthan gum to the skin care composition to form a stabilized skin care composition. Embodiment 96 is the method of Embodiments 94 to 95, wherein the stabilized skin care composition has a pH of 10 or greater, or wherein an intermediate formulation comprising the attapulgite clay, polyurethane-39, and *Acacia senegal* gum-encapsulated xanthan gum and used to form the stabilized skin care composition has a pH of 10 or greater. Embodiment 97 is the method of Embodiments 94 to 96, wherein the stabilized skin care composition is stable after one or more freeze and thaw. Embodiment 98 is the method of Embodiments 94 to 97, wherein the stabilized skin care composition is the composition of any one of Embodiments 57 to 74.

Embodiment 99 is a method of stabilizing a skin care composition comprising adding magnesium aluminum silicate, sodium polystyrene sulfonate, and xanthan gum to a skin care composition to form a stabilized skin care composition. Embodiment 100 is the method of Embodiment 99, wherein the method comprises adding from about 0.2 to 20% by weight of magnesium aluminum silicate, from about 0.2 to 20% by weight of sodium polystyrene sulfonate, and from about 0.02 to 2% by weight of xanthan gum to the skin care composition to form a stabilized skin care composition. Embodiment 101 is the method of Embodiments 99 to 100, wherein the stabilized skin care composition has a pH of 10 or greater, or wherein an intermediate formulation comprising the magnesium aluminum silicate, sodium polystyrene sulfonate, and xanthan gum and used to form the stabilized skin care composition has a pH of 10 or greater. Embodiment 102 is the method of Embodiments 99 to 101, wherein the stabilized skin care composition is stable after one or more freeze and thaw. Embodiment 103 is the method of Embodiments 99 to 102, wherein the stabilized skin care composition is the composition of any one of Embodiments 75 to 89.

"Topically applying" means to apply a composition onto the surface of skin. Such compositions are typically dermatologically-acceptable in that they do not have undue toxicity, incompatibility, instability, allergic response, and the like, when applied to skin. Topical skin care compositions of the present invention can be formulated to achieve a targeted dissolution to avoid significant dripping after application to skin.

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations are refers to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase or production of elastin to achieve a desired result.

The term "effective," as that term is used in the specification and/or claims, means adequate to accomplish a desired, expected, or intended result.

The use of the word "a" or "an" when used in conjunction with the terms "comprising," "including," "having," or "containing," or any variations of these terms, in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the phrase "consisting essentially of," a basic and novel property of the compositions and method of the present invention is a composition containing magnesium aluminum silicate, xanthan gum, and sodium polystyrene sulfonate. Another novel property of the compositions and methods is the use of the compositions to improve skin feel, soften skin, and attract and retain moisture.

As used herein, "treatment" means to improve a condition or appearance of the skin either temporarily or permanently. When the compositions are administered to the skin, the compositions may improve skin feel, soften skin, and attract and/or retain moisture.

Other objects, features, and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION

Figure 1A:
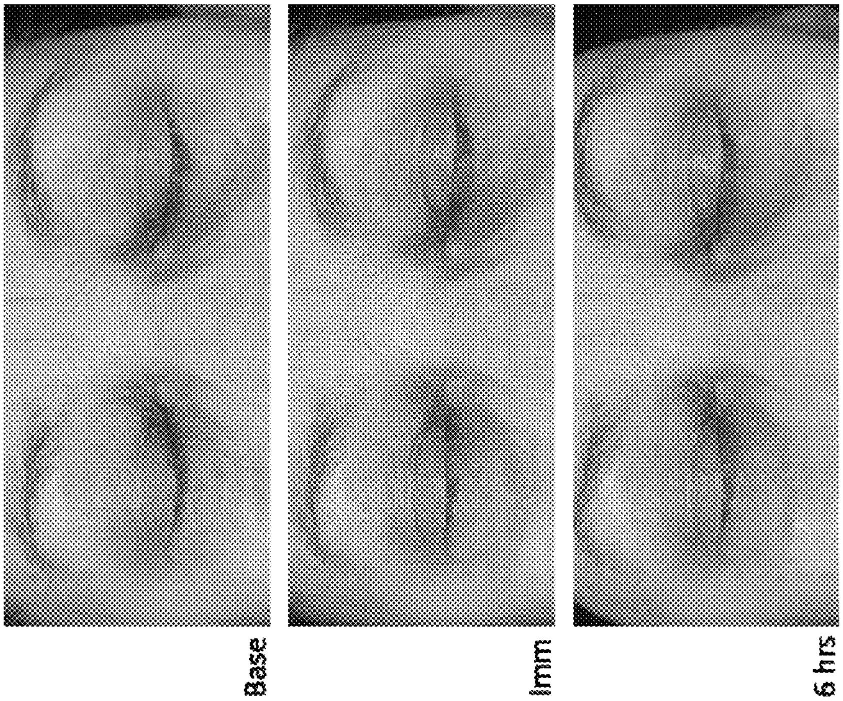
FIGS. 1A-1B: Before and after pictures of skin around the eyes (periorbital region) of two clinical subjects' that has been treated with a combination of sodium silicate, sodium polystyrene sulfonate, carrageenan, *Acacia senegal* gum-encapsulated xanthan gum, xanthan gum, and *Cyamopsis tetragonoloba* (guar) gum. Pictures were taken before (base), immediately after (Imm), and six hours after application of the composition (6 hrs).

The area underneath the eyes is prone to issues not felt by skin on other parts of the body. Although all areas of the skin are subject to wrinkling and dryness, the area under the eye is particularly susceptible to wrinkling and dryness. This is due to fewer oil glands in comparison to other areas of skin, which adds to the unique skin problems around the eye. The heightened sensitivity of the skin under the eye can also be exacerbated by environmental influences, including lifestyle choices and external impacts.

Numerous active agents including humectants, emollients, and moisturizers are used to add moisture to the skin. Other ingredients are also known to have some limited beneficial value in preventing premature wrinkling. However, many existing compositions represent a tradeoff between pleasing texture and stability over time. The inventors have developed a method of stabilizing a skin care composition that extends the amount of time over which the composition maintains its initial rheological properties. The stabilizing method entails adding a unique combination of rheology-modifying agents to a skin care composition. The present inventors have also developed a method and compositions for improving the appearance of skin under the eyes by use of a composition that exhibits good skin feel and maintains its pleasing texture over time.

A. Primary Ingredients

The composition disclosed herein is useful for treating skin underneath the eye and comprises a novel combination of rheology modifiers and skin active agents. The cosmetic composition obtained may be stable for several months, even when it is subjected to variations in temperature. The cosmetic skin care compositions reduce puffiness and/or crepiness, reduce under eye lines, and improve skin feel, soften skin, and attract and retain moisture.

The combination of a sodium silicate, sodium polystyrene sulfonate, carrageenan, *Acacia senegal* gum-encapsulated xanthan gum, xanthan gum, and *Cyamopsis tetragonoloba* (guar) gum reduces puffiness and/or crepiness, reduces under eye lines, and improves skin feel, softens skin, and attracts and retains moisture. Sodium silicate is an astringent substance that tends to shrink or constrict the skin. Sodium polystyrene sulfonate is a high molecular weight composition that forms clear, a flexible film that shrinks upon drying to tighten skin and smooth fine lines and wrinkles. Natural gums including carrageenan, *Acacia senegal* gum, xanthan gum, and *Cyamopsis tetragonoloba* (guar) gum can improve skin feel, soften skin, and attract and retain moisture and may also be film-formers to tighten skin and smooth fine lines and wrinkles.

The combination of magnesium aluminum silicate, xanthan gum, and sodium polystyrene sulfonate serves as a functional vehicle to which additional skin-benefiting components are added. Magnesium aluminum silicate is a particulate composition that serves as a viscosity-increasing agent, and is also used to aid in suspension of other components within a composition. Xanthan gum is also a thickening agent that increases viscosity. In contrast to the particulate magnesium aluminum silicate, xanthan gum is a polysaccharide with short side chains. Sodium polystyrene sulfonate is a polymer that serves as a viscosity-increasing thickening agent. The combination of magnesium aluminum silicate, polymeric xanthan gum and sodium polystyrene sulfonate thickening agents provides a personal care composition with enhanced stability and shelf life. The combination of magnesium aluminum silicate, polymeric xanthan gum and sodium polystyrene sulfonate serves as a functional vehicle to which additional skin-benefiting components are added.

The combination of attapulgite clay, hydroxyethyl acrylate/sodium acryloyldimethyl taurate copolymer, and *Acacia* gum-encapsulated xanthan gum serves as an unexpectedly stable functional vehicle to which additional skin-benefiting components are added. The combination of attapulgite clay, polyurethane-39, and *Acacia* gum-encapsulated xanthan gum serves as an unexpectedly stable functional vehicle to which additional skin-benefiting components are added. Attapulgite clay increases viscosity by thickening a composition and increases the shelf life of an emulsion. Polyurethane-39 is a urethane-based rheology modifier. It is used as a thickening agent and exhibits high thickening efficiency under high salt concentrations and a broad range of pH values. Hydroxyethyl acrylate/sodium acryloyldimethyl taurate copolymer is formulated as a liquid polymer produced by inverse emulsion polymerization. It is used as a thickener, stabilizer, and/or texturizer and provides a melting skin feel. *Acacia* gum-encapsulated xanthan gum is used as a thickening agent that does not impart a stringy effect when used in aqueous dispersions or gels. The combinations of attapulgite clay, hydroxyethyl acrylate/sodium acryloyldimethyl taurate copolymer, and *Acacia* gum-encapsulated xanthan gum and attapulgite clay, polyurethane-39, and *Acacia* gum-encapsulated xanthan gum provide structure and enhanced stability to a personal care composition. It was surprisingly found that the combination of attapulgite clay, hydroxyethyl acrylate/sodium acryloyldimethyl taurate copolymer, and *Acacia* gum-encapsulated xanthan gum in a topical formulation has increased stability, such as at high pH and during freeze/thaw cycles, when compared to formulations using magnesium aluminum silicate instead of the combination of attapulgite clay, polyurethane-39, and *Acacia* gum-encapsulated xanthan gum. It was surprisingly found that the combination of attapulgite clay, polyurethane-39, and *Acacia* gum-encapsulated xanthan gum in a topical formulation has increased stability, such as at high pH and during freeze/thaw cycles, when compared to formulations using magnesium aluminum silicate instead of the combination of attapulgite clay, polyurethane-39, and *Acacia* gum-encapsulated xanthan gum.

Attapulgite clay, hydroxyethyl acrylate/sodium acryloyldimethyl taurate copolymer, and *Acacia* gum-encapsulated xanthan gum may be used in combination with magnesium aluminum silicate, polymeric xanthan gum, and sodium polystyrene sulfonate to provide additional stability. The combination of attapulgite clay, hydroxyethyl acrylate/sodium acryloyldimethyl taurate copolymer, *Acacia* gum-encapsulated xanthan gum, polymeric xanthan gum, magnesium aluminum silicate, and sodium polystyrene sulfonate may serve as a functional vehicle to which additional skin-benefiting components may be added.

Attapulgite clay, polyurethane-39, and *Acacia* gum-encapsulated xanthan gum may be used in combination with magnesium aluminum silicate, polymeric xanthan gum, and sodium polystyrene sulfonate to provide additional stability. The combination of attapulgite clay, polyurethane-39, *Acacia* gum-encapsulated xanthan gum, polymeric xanthan gum, magnesium aluminum silicate, and sodium polystyrene sulfonate may serve as a functional vehicle to which additional skin-benefiting components may be added.

In some aspects, the additional skin-benefiting components are selected from the group consisting of an alkyl glycol, sodium silicate, phenoxyethanol, carrageenan, mica, titanium dioxide, EDTA, iron oxides, ethylhexylglycerin, tocopherol, polysorbate 20, polyisobutene, polyacrylate-13, sodium sulfate, *Cyamopsis tetragonoloba* (guar) gum, sorbitan isostearate, and combinations thereof.

B. Amounts of Ingredients

It is contemplated that the compositions of the present invention can include any amount of the ingredients discussed in this specification. The compositions can also include any number of combinations of additional ingredients described throughout this specification (e.g., pigments, or additional cosmetic or pharmaceutical ingredients). The concentrations of the ingredients within the compositions can vary. In non-limiting embodiments, for example, each of retinol and ascorbic acid can independently comprise, consist essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4% 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

C. Vehicles

The compositions of the present invention can include or be incorporated into all types of vehicles and carriers. The vehicle or carrier can be a pharmaceutically or dermatologically acceptable vehicle or carrier. Non-limiting examples of vehicles or carriers include water, glycerin, alcohol, oil, a silicon containing compound, a silicone compound, and wax. Variations and other appropriate vehicles will be apparent to the skilled artisan and are appropriate for use in the present invention. In certain aspects, the concentrations and combinations of the compounds, ingredients, and agents can be selected in such a way that the combinations are chemically compatible and do not form complexes which precipitate from the finished product.

D. Structure

The compositions of the present invention can be structured or formulated into a variety of different forms. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, pastes, solutions (both aqueous and hydro-alcoholic), anhydrous bases (such as lipsticks and powders), gels, masks, scrubs, body butters, peels, and ointments. Variations and other structures will be apparent to the skilled artisan and are appropriate for use in the present invention.

E. Additional Ingredients

In addition to the combination of ingredients disclosed by the inventors, the compositions can also include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrance agents (artificial and natural; e.g., gluconic acid, phenoxyethanol, and triethanolamine), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), flavoring agents/aroma agents (e.g., *Stevia rebaudiana* (sweetleaf) extract, and menthol), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as para-aminobenzoic acid ("PABA") and corresponding PABA derivatives, titanium dioxide, zinc oxide, etc.), essential oils, vitamins (e.g., B, D, E, and K), trace metals (e.g., zinc, calcium and selenium), anti-irritants (e.g., steroids and non-steroidal anti-inflammatories), botanical extracts (e.g., *Aloe vera*, chamomile, cucumber extract, *Ginkgo biloba, ginseng*, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, methyl gluceth-20, saccharide isomerate, and mannitol), exfoliants, waterproofing agents (e.g., magnesium/aluminum hydroxide stearate), skin conditioning agents (e.g., *Aloe* extracts, allantoin, bisabolol, ceramides, dimethicone, hyaluronic acid, biosaccharide gum-1, ethylhexylglycerin, pentylene glycol, hydrogenated polydecene, octyldodecyl oleate, and dipotassium glycyrrhizate). Non-limiting examples of some of these ingredients are provided in the following subsections.

a. UV Absorption and/or Reflecting Agents

UV absorption and/or reflecting agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate (octinoxate), isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrrolidone carboxylic acid, potassium PCA, propylene glycol, saccharide isomerate, sodium glucuronate, sodium PCA, sorbitol, sucrose, trehalose, urea, and xylitol.

Other examples include acetylated lanolin, acetylated lanolin alcohol, alanine, algae extract, *Aloe barbadensis, Aloe barbadensis* extract, *Aloe barbadensis* gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamom (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, *Geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, *Glycine*, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, *Macadamia ternifolia* nut oil, maltitol, matricaria (*Chamomilla recutita*) oil, methyl glucose sesquistearate, methylsilanol PCA, mineral oil, mink oil, mortierella oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*Mentha piperita*) oil, petrolatum, phospholipids, plankton extract, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang (*Cananga odorata*) oil.

c. Antioxidants

Additional antioxidants can be used in combination with ascorbic acid and vitamin E. Non-limiting examples of antioxidants that can be used include acetyl cysteine, ascorbic acid derivatives like ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agents, in certain aspects, assist in providing rheological characteristics to the composition that contribute to stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Michigan. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Michigan.

g. Exfoliating Agent

Exfoliating agents include ingredients that remove dead skin cells on the skin's outer surface. These agents may act through mechanical, chemical, and/or other means. Non-limiting examples of mechanical exfoliating agents include abrasives such as pumice, silica, cloth, paper, shells, beads, solid crystals, solid polymers, etc. Non-limiting examples of chemical exfoliating agents include acids and enzyme exfoliants. Acids that can be used as exfoliating agents include, but are not limited to, glycolic acid, lactic acid, citric acid, alpha hydroxy acids, beta hydroxy acids, etc. Other exfoliating agents known to those of skill in the art are also contemplated as being useful within the context of the present invention.

h. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, *Macadamia* nut oil, tea tree oil, evening primrose oil, Spanish sage oil, Spanish rosemary oil, coriander oil, thyme oil, *Pimento* berries oil, rose oil, anise oil, balsam oil, bergamot oil, rosewood oil, cedar oil, chamomile oil, sage oil, clary sage oil, clove oil, cypress oil, *Eucalyptus* oil, fennel oil, sea fennel oil, frankincense oil, *Geranium* oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang. Other essential oils known to those of skill in the art are also contemplated as being useful within the context of the present invention.

i. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyltaurate/vp copolymer, or a mixture of them.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerythritol (e.g., CARBOPOL™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three units.

Non-limiting examples of gums that can be used with the present invention include *Acacia*, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

j. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal, or combinations thereof.

k. Emollients

Useful emollients include the following: (a) silicone oils and modifications thereof such as linear and cyclic polydimethylsiloxanes; amino, alkyl, alkylaryl, and aryl silicone oils; (b) fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride; (c) waxes such as carnauba, spermaceti, beeswax, lanolin, and derivatives thereof, (d) hydrophobic plant extracts; (e) hydrocarbons such as liquid paraffins, vaseline, microcrystalline wax, ceresin, squalene, pristan and mineral oil; (f) higher fatty acids such as lauric, myristic, palmitic, stearic, behenic, oleic, linoleic, linolenic, lanolic, isostearic, arachidonic and poly unsaturated fatty acids (PUFA); (g) higher alcohols such as lauryl, cetyl, stearyl, oleyl, behenyl, cholesterol and 2-hexydecanol alcohol; (h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; (i) essential oils and extracts thereof such as *Mentha*, jasmine, camphor, white cedar, bitter orange peel, ryu, turpentine, cinnamon, bergamot, *Citrus* unshiu, calamus, pine, lavender, bay, clove, hiba, *Eucalyptus*, lemon, starflower, thyme, peppermint, rose, sage, sesame, ginger, basil, juniper, lemon grass, rosemary, rosewood, avocado, grape, grapeseed, myrrh, cucumber, watercress, *Calendula*, elder flower, *Geranium*, linden blossom, amaranth, seaweed, ginko, ginseng, carrot, guarana, tea tree, jojoba, comfrey, oatmeal, cocoa, neroli, vanilla, green tea, penny royal, *Aloe vera*, menthol, cineole, eugenol, citral, citronelle, borneol, linalool, geraniol, evening primrose, camphor, thymol, spirantol, penene, limonene and terpenoid oils; (j) lipids such as cholesterol, ceramides, sucrose esters and pseudo-ceramides as described in European Patent Specification No. 556,957; (k) vitamins, minerals, and skin nutrients such as vitamins A, E, and K; vitamin alkyl esters, including vitamin C alkyl esters; magnesium, calcium, and milk; (l) sunscreens such as octyl methoxyl cinnamate (Parsol MCX) and butyl methoxy benzoylmethane (Parsol 1789); (l) phospholipids; (m) polyhydric alcohols such as glycerine and propylene glycol; and polyols such as polyethylene glycols; (n) antiaging compounds such as alpha hydroxy acids, beta hydroxy acids; and (o) mixtures of any of the foregoing components, and the like.

l. Tackifiers

Examples of suitable tackifiers, include, but are not limited to, aliphatic hydrocarbon resins, aromatic modified aliphatic hydrocarbon resins, hydrogenated polycyclopentadiene resins, polycyclopentadiene resins, gum rosins, gum rosin esters, wood rosins, wood rosin esters, tall oil rosins, tall oil rosin esters, polyterpenes, aromatic modified polyterpenes, terpene phenolics, aromatic modified hydrogenated polycyclopentadiene resins, hydrogenated aliphatic resin, hydrogenated aliphatic aromatic resins, hydrogenated terpenes and modified terpenes, hydrogenated rosin acids, hydrogenated rosin esters, polyisoprene, partially or fully hydrogenated polyisoprene, polybutenediene, partially or fully hydrogenated polybutenediene, and the like. As is evidenced by some of the cited examples, the tackifier may be fully or partially hydrogenated. The tackifier may also be non-polar. (Non-polar meaning that the tackifier is substantially free of monomers having polar groups. Preferably, the polar groups are not present, however, if they are present, they are preferably present in an amount of up to about 5% by weight, preferably up to about 2% by weight, and more preferably up to about 0.5% by weight).

m. Colorant

The compositions of the present invention also contain at least one cosmetically acceptable colorant such as a pigment or dyestuff. Examples of suitable pigments include, but are not limited to, inorganic pigments, organic pigments, lakes, pearlescent pigments, iridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

n. Surfactant

Surfactants useful as the surfactant components in the compositions of the present invention include nonionic, anionic, cationic, and amphoteric (zwitterionic) surfactants and may be used in combination with each other.

o. pH Adjustors

The pH adjustors, include inorganic and organic acids and bases and in particular aqueous ammonia, citric acid, phosphoric acid, acetic acid, sodium hydroxide, lactic acid, levulinic acid, glycolic acid, tartaric acid, malic acid, pyrrolidonecarboxylic acid (PCA), succinic acid, citric acid, glutamic acid, 2-amino-2-methyl-1-propanol (AMP), and triethanolamine (TEA).

p. Reducing Agents

Suitable reducing agents include, but are not limited to, thiourea, salts (such as sodium salts) of thiosulfate, sulfite, bisulfite, metabisulfite, borohydride, and hypophosphite, ascorbic acid and salts, esters, and derivatives thereof (e.g., ascorbyl palmitate and ascorbyl polypeptide), and tocopherols and salts, esters, and derivatives thereof (e.g., tocopherol acetate). Other reducing agents are listed on pages 1655-56 of the INCI Handbook.

q. Fragrances

The compositions disclosed herein may optionally include a fragrance. Examples of possible fragrances include natural oils or naturally derived materials, and synthetic fragrances such as hydrocarbons, alcohols, aldehydes, ketones, esters, lactones, ethers, nitriles, and polyfunctionals. Non-limiting examples of natural oils include the following: basil (*Ocimum basilicum*) oil, bay (*Pimento acris*) oil, bee balm (*Monarda didyma*) oil, bergamot (*Citrus aurantium bergamia*) oil, cardamom (*Elettaria cardamomum*) oil, cedarwood (*Cedrus atlantica*) oil, chamomile (*Anthemis nobilis*) oil, cinnamon (*Cinnamomum cassia*) oil, citronella (*Cymbopogon nardus*) oil, clary (*Salvia sclarea*) oil, clove (*Eugenia caryophyllus*) oil, cloveleaf (*Eufenia caryophyllus*) oil, *Cyperus esculentus* oil, cypress (*Cupressus sempervirens*) oil, *Eucalyptus citriodora* oil, *Geranium maculatum* oil, ginger (*Zingiber officinale*) oil, grapefruit (*Citrus grandis*) oil, hazel (*Corylus avellana*) nut oil, jasmine (*Jasminum officinale*) oil, *Juniperus communis* oil, *Juniperus oxycedrus* tar, *Juniperus virginiana* oil, kiwi (*Actinidia chinensis*) water, lavandin (*Lavandula hybrida*) oil, lavender (*Lavandula angustifolia*) oil, lavender (*Lavandula angustifolia*) water, lemon (*Citrus medica limonum*) oil, lemongrass (*Cymbopogon schoenanthus*) oil, lime (*Citrus aurantifolia*) oil, linden (*Tilia cordata*) oil, linden (*Tilia cordata*) water, mandarin orange (*Citrus nobilis*) oil, nutmeg (*Myristica fragrans*) oil, orange (*Citrus aurantium dulcis*) flower oil, orange (*Citrus aurantium dulcis*) oil, orange (*Citrus aurantium dulcis*) water, patchouli (*Pogostemon cablin*) oil, peppermint (*Menthe piperita*) oil, peppermint (*Menthe peperita*) water, rosemary (*Rosmarinus officinalis*) oil, rose oil, rose (*Rosa damascena*) extract, rose (*Rosa multiflora*) extract, rosewood (*Aniba rosaeodora*) extract, sage (*Salvia officinalis*) oil, sandalwood (*Santalum album*) oil, spearmint (*Menthe viridis*) oil, tea tree (*Melaleuca alternifolia*) oil, and ylang (*Cananga odorata*) oil. Some non-limiting examples of synthetic hydrocarbon fragrances include caryophyllene, β-farnesene, limonene, α-pinene, and, β-pinene. Some non-limiting examples of synthetic alcohol fragrances include bacdanol, citronellol, linalool, phenethyl alcohol, and α-terpineol (R=H). Some non-limiting examples of synthetic aldehyde fragrances include 2-methyl undecanal, citral, hexyl cinnamic aldehyde, isocycolcitral, lilial, and 10-undecenal. Some non-limiting examples of synthetic ketone fragrances include cashmeran, α-ionone, isocyclemone E, koavone, muscone, and tonalide. Some non-limiting examples of synethetic ester fragrances include benzyl acetate, 4-t-butylcyclohexyl acetate (cis and trans), cedryl acetate, cyclacet, isobornyl acetate, and α-terpinyl acetate (R=acetyl). Some non-limiting examples of synthetic lactone fragrances include coumarin, jasmine lactone, muskalactone, and peach aldehyde. Some non-limiting examples of synthetic ether fragrances include ambroxan, anther, and galaxolide. Some non-limiting examples of synthetic nitrile fragrances include cinnamonitrile and gernonitrile. Finally, some non-limiting examples of synthetic polyfunctional fragrances include amyl salicylate, isoeugenol, hedione, heliotropine, lyral, and vanillin.

r. Foaming Agents

The foaming agents include, for example, sodium lauryl sulfate, sodium lauroyl sarcosine, sodium alkyl sulfosuccinates, sodium coconut oil fatty acid monoglycerol sulfonates, sodium α-olefin sulfonates, N-acylamino acid salts such as N-acyl glutamate, 2-alkyl-N-carboxymethyl-N-hydroxyethylimidazolinium betaine, maltitol fatty acid esters, sucrose fatty acid esters, polyglycerol fatty acid esters, fatty acid diethanolamides, polyoxyethylene sorbitan monostearate, polyoxyethylene hydrogenated castor oil and polyoxyethylene fatty acid esters. These foaming agents are usable either alone or in combination of two or more of them.

s. Tanning Agents

Suitable tanning agents include, without limitation, alpha-hydroxy aldehydes and ketones, glyceraldehyde and related alcohol aldehydes, various indoles, imidazoles and derivatives thereof, and various approved pigmentation agents. Other suitable tanning agents include, without limitation, methyl glyoxal, glycerol aldehyde, erythrulose, alloxan, 2,3-dihydroxysuccindialdehyde, 2,3-dimethoxysuccindialdehyde, 2-amino-3-hydroxysuccindialdehyde and 2-benzylamino-3-hydroxysuccindialdehyde.

t. Astringents

Suitable astringents include, without limitation, aluminum citrate, aluminum lactate, extracts of birch, extracts of coffee, extracts of evening primrose, extracts of grape, extracts of henna, extracts of ivy, extracts of lemon, extracts of witch hazel, Ammonium and Potassium Alum, Aluminum Triphosphate, Aluminum Glycinate and Aluminum Phenolsulfate, Alcloxa, Aldioxa, Aluminum Stearate, Aluminum Sulfate and Aluminum Citrate, Sodium Aluminum Phosphate, Sodium Alum, Sodium Aluminum Chlorohydroxy Lactate, Calcium Lactate, Calcium Chloride, Calcium Sulfate Hydrate, Sodium Aluminum Lactate, Zinc Acetate, Zinc Chloride, Zinc Sulfate, Zinc Lactate, Zinc Zeolite, Zinc Phenolsulfonate, and combinations thereof. What is meant by an extract is either the whole fruit, bean, and/or plant or select constituents of such fruit, bean, and/or plant.

u. Antiseptics

Suitable antiseptics include, without limitation, methyl, ethyl, propyl, or butyl ester of p-oxybenzoic acid, phenoxyethanol, o-phenylphenol, dehydroacetic acid, or salts thereof, p-cresol, m-cresol, o-chlor-m-xylenol, peppermint oil, *Echinacea*, bloodroot, cayenne, tea tree oil, wild bergamont, chaparral, stinging metal, bay, myrrh, rhatany bark, toothache tree, *Calendula*, chamomile, mupirocin, neomycin sulfate, bacitracin, polymyxin B, l-ofloxacin, tetracyclines (chlortetracycline hydrochloride, oxytetracycline hydrochloride and tetracycline hydrochoride), clindamycin phosphate, gentamicin sulfate, benzalkonium chloride, benzethonium chloride, hexylresorcinol, methylbenzethonium chloride, phenol, quaternary ammonium compounds, triclocarban, triclosan, and tea tree oil.

v. Deodorants and Antiperspirants

Suitable antiperspirants and deodorants include, without limitation, zinc salts such as zinc sulfate and zinc chloride, glycinates such as aluminum zirconium glycinate, aluminum chlorohydrate, aluminum zirconium tetrachlorohydrex, zinc carbonate, orthophenylphenol, and quaternary ammonium compounds such as dimethyl benzyl ammonium chloride and hexamethonium chloride.

w. Lighteners

Examples of skin lighteners include, without limitation, hydroquinone, kojic acid, licorice and/or its derivatives, ascorbic acid and/or its derivatives, arbutin, bearberry extract, *Glycyrrhiza glabra* and its derivatives, *Chlorella vulgaris* extract, *perilla* extract, coconut fruit extract, and/or other depigmenting agents.

x. Biocides

Examples of biocides include, without limitation, triclosan, 3,4,4'-trichlorocarbanilide (triclocarban); 3,4,4'-trifluoromethyl-4,4'-dichlorocarbanilide (cloflucarban); 5-chloro-2-methyl-4-isothiazolin-3-one; iodopropynlbutylcarbamate; 8-hydroxyquinoline; 8-hydroxyquinoline citrate; 8-hydroxyquinoline sulfate; 4-chloro-3,5-xylenol(chloroxylenol); 2-bromo-2-nitropropane-1,3-diol; diazolidinyl urea; butoconazole; nystatin; terconazole; nitrofurantoin; phenazopyridine; acyclovir; clortrimazole; chloroxylenol; chlorhexidine; miconazole; terconazole; butylparaben; ethylparaben; methylparaben; methylchloroisothiazoline; methylisothiazoline; a mixture of 1,3-bis(hydroxymethyl)-5,5-dimethylhydantoin and 3-iodo-2-propynyl butyl carbamate; oxyquinoline; EDTA; tetrasodium EDTA; p-hydroxyl benzoic acid ester; alkyl pyridinum compounds; coco phosphatidyl PG-dimonium chloride; chlorhexidine gluconate; chlorhexidine digluconate; chlorhexidine acetate; chlorhexidine isethionate; chlorhexidine hydrochloride; benzalkonium chloride; benzethonium chloride; polyhexamethylene biguanide; and mixtures thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, anti-seborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, photosensitizing actives, skin protectant/barrier agents, steroids including hormones and corticosteroids, sunburn treatment agents, sunscreens, transdermal actives, wart treatment agents, wound treatment agents, wound healing agents, etc.

E. Kits

Kits are also contemplated as being used in certain aspects of the present invention. For instance, compositions of the present invention can be included in a kit. A kit can include a container. Containers can include an ampoule, a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

The ingredients in Table 1 were used in the formulations and methods described below.

TABLE 1

| Ingredient(s) | Trade Name | Supplier |
|---|---|---|
| Attapulgite clay | PHARMASORB ® | BASF |
| Magnesium aluminum silicate | VEEGUM ® HV | Vanderbilt Minerals, Inc |
| *Acacia Senegal* gum & Xanthan gum | SOLAGUM ™ AX | Seppic |
| Carrageenan | GENUVISCO ® Carrageenan CG-131 | CP Kelco |
| Xanthan Gum | | CP Kelco |
| *Cyamopsis tetragonoloba* (guar) gum | JAGUAR ® S | Solvay |
| Sodium polystyrene sulfonate & Sodium sulfate | FLEXAN ® II | Nouryon |
| Mica<br>Titanium dioxide<br>Iron oxides | ELDORADO ™ Red Gold/MGM-307 | Sandream Impact |

TABLE 1-continued

| Ingredient(s) | Trade Name | Supplier |
|---|---|---|
| Phenoxyethanol Ethylhexylglycerin | EUXYL ® PE 9010 | Schülke |
| Hydroxyethyl Acrylate/Sodium Acryloyldimethyl Taurate Copolymer | SIMULGEL ™ I-NS 100 | Seppic |
| Sodium silicate | | PQ Corp |

Example 2

Formulations having the ingredients from Example 1 were prepared as topical skin compositions according to the current disclosure. The formulations in Tables 2-6 provide examples of cosmetic compositions according to the current disclosure.

In some embodiments, the formulations in Tables 2-6 are prepared according to the following process. First, in a suitable container fitted with appropriate mixing elements, combine water and a chelating agent and mix appropriated until homogeneous. Then, add attapulgite clay and magnesium aluminum silicate to the container, hydrating and dispersing the attapulgite clay and magnesium aluminum silicate via thermal and/or shear energy input. Once the attapulgite clay and magnesium aluminum silicate are fully hydrated and dispersed, add an alkyl glycol (e.g., butylene glycol, propanediol) and/or one or more natural gums (e.g., *Acacia senegal* gum, xanthan gum, carrageenan, *Cyamopsis tetragonoloba* (guar) gum) to the container, adjusting the addition rate as necessary to minimize clumping of the natural gums. Alternatively, the natural gums may be premixed with the alkyl glycol prior to addition to the container. Next, hydrate and disperse the natural gums via thermal and/or shear energy input. Once the natural gums are fully hydrated and dispersed, cool the mixture to <65° C. Then, add and incorporate sodium polystyrene sulfate, pearl, and/or mica, fully hydrating and dispersing the sodium polystyrene sulfate, pearl, and/or mica via thermal and/or shear energy input. Once the sodium polystyrene sulfate, pearl, and/or mica are fully hydrated and dispersed, add and incorporate one or more of preservative(s), polyurethane, and/or polymeric thickener (S) with appropriate mixing and/or shear energy input. Once homogenous, cool the mixture to <35° C. Then, add sodium silicate at a suitable controlled rate, and incorporate the sodium silicate with appropriate mixing and/or shear energy input. Once the mixture is homogeneous, remove entrapped air via vacuum.

TABLE 2

| Ingredient | % Concentration (by weight) |
|---|---|
| Magnesium aluminum silicate | 4.5 |
| Sodium polystyrene sulfate | 4.5 |
| Butylene glycol | 2.0 |
| Sodium silicate | 1.875 |
| Polyacrylate-13 | 0.64 |
| Phenoxyethanol | 0.45 |
| Polyisobutene | 0.27 |
| Sodium sulfate | 0.25 |
| Carrageenan | 0.2 |
| Xanthan gum | 0.2 |
| Mica | 0.1475 |
| Titanium dioxide | 0.0525 |
| Disodium EDTA | 0.05 |
| Iron oxides | 0.05 |
| Ethylhexylglycerin | 0.04998 |
| Polysorbate 20 | 0.045 |

TABLE 2-continued

| Ingredient | % Concentration (by weight) |
|---|---|
| Tocopherol | 0.00002 |
| Excipients* | q.s. |

*Excipients can be added, for example, to modify the rheological properties of the composition. Alternatively, the amount of water can be varied so long as the amount of water in the composition is at least 60% w/w, and preferably between 60 to 95% w/w.

TABLE 3

| Ingredient | % Concentration (by weight) |
|---|---|
| Magnesium aluminum silicate | 3.5 |
| Sodium polystyrene sulfate | 2.7 |
| Butylene glycol | 2.0 |
| Sodium silicate | 1.875 |
| Phenoxyethanol | 0.45 |
| Carrageenan | 0.2 |
| Xanthan gum | 0.2 |
| Sodium sulfate | 0.15 |
| Mica | 0.1475 |
| Titanium dioxide | 0.0525 |
| Disodium EDTA | 0.05 |
| Iron oxides | 0.05 |
| Ethylhexylglycerin | 0.04998 |
| Tocopherol | 0.00002 |
| Excipients | q.s. |

* Excipients can be added, for example, to modify the rheological properties of the composition. Alternatively, the amount of water can be varied so long as the amount of water in the composition is at least 60% w/w, and preferably between 60 to 95% w/w.

TABLE 4

| Ingredient | % Concentration (by weight) |
|---|---|
| Magnesium aluminum silicate | 4.5 |
| Sodium polystyrene sulfate | 4.5 |
| Propanediol | 2.0 |
| Sodium silicate | 1.875 |
| Phenoxyethanol | 0.45 |
| Sodium sulfate | 0.25 |
| Carrageenan | 0.2 |
| Xanthan gum | 0.2 |
| Mica | 0.1475 |
| Titanium dioxide | 0.0525 |
| Disodium EDTA | 0.05 |
| Iron oxides | 0.05 |
| Ethylhexylglycerin | 0.04998 |
| Tocopherol | 0.00002 |
| Excipients | q.s. |

* Excipients can be added, for example, to modify the rheological properties of the composition. Alternatively, the amount of water can be varied so long as the amount of water in the composition is at least 60% w/w, and preferably between 60 to 95% w/w.

TABLE 5

| Ingredient | % Concentration (by weight) |
|---|---|
| Disodium EDTA | 0.05 |
| Attagel 50 (Attapulgite Clay) | 4.5 |
| Magnesium aluminum silicate | 3.5 |
| Solagum AX (*Acacia Senegal* gum-encapsulated xantham gum) | 0.4 |
| Xanthan gum | 0.2 |
| Carrageenan | 0.2 |
| Butylene glycol | 2.0 |
| Flexan II Polymer (sodium polystyrene sulfate) | 3.0 |
| Eldorado Red Gold (mica, titanium dioxide, and iron oxides) | 0.25 |
| EUXYL PE 9010 (phenoxyethanol and ethylhexylglycerin) | 0.5 |

TABLE 5-continued

| Ingredient | % Concentration (by weight) |
|---|---|
| Luvigel Star AT3 (Polyurethane-39) | 2.0 |
| Water & Sodium silicate | 5.0 |
| Excipients | q.s. |

* Excipients can be added, for example, to modify the rheological properties of the composition. Alternatively, the amount of water can be varied so long as the amount of water in the composition is at least 60% w/w, and preferably between 60 to 95% w/w.

TABLE 6

| Ingredient | % Concentration (by weight) |
|---|---|
| Magnesium Aluminum Silicate | 4.5 |
| Sodium Polystyrene Sulfonate | 2.7 |
| Butylene Glycol | 2.0 |
| Sodium Silicate | 1.875 |
| Attapulgite | 1.0 |
| Xanthan Gum | 0.4975 |
| Phenoxyethanol | 0.45 |
| *Acacia Senegal* gum | 0.3605 |
| Carrageenan | 0.3 |
| Sodium Sulfate | 0.15 |
| Mica | 0.1475 |
| *Cyamopsis tetragonoloba* (Guar) Gum | 0.093 |
| Hydroxyethyl Acrylate/Sodium Acryloyldimethyl Taurate Copolymer | 0.075 |
| Titanium Dioxide | 0.0525 |
| Isohexadecdane | 0.051 |
| Disodium EDTA | 0.05 |
| Iron Oxides | 0.05 |
| Ethylhexylglycerin | 0.04998 |
| Polysorbate 60 | 0.011 |
| Sorbitan Isostearate | 0.004 |
| Tocopherol | 0.00002 |
| Excipients | q.s. |

* Excipients can be added, for example, to modify the rheological properties of the composition. Alternatively, the amount of water can be varied so long as the amount of water in the composition is at least 60% w/w, and preferably between 60 to 95% w/w.

Example 2

Stability Testing

The experiments below can be conducted to test how well the cosmetic compositions disclosed herein resist common stresses such as temperature extremes and physical agitation.

Temperature Variations: High temperature testing can be used as a predictor of long-term stability. The tests can be performed at various temperatures, including 37° C. (98° F.) and 45° C. (113° F.). The cosmetic compositions can be stored at 45° C. for three months and examined after the storage period. The compositions are expected to exhibit acceptable stability after high temperature testing and storage. This translates to storage-stability at room temperature for two years.

Cycle Testing: The compositions can be subjected to three cycles of temperature testing from −10° C. (14° F.) to 25° C. (77° F.). The compositions can be placed at −10° C. for 24 hours, then placed at room temperature (25° C.) for 24 hours. This represents one cycle. Rheological properties of the compositions can then be examined. The compositions are expected to successfully pass three cycles, thereby establishing the stability of the compositions when subjected to multiple changes in temperature.

Centrifuge Testing: The dispersed phase (of an oil-in-water emulsion) has a tendency to separate and rise to the top of the emulsion forming a layer of oil droplets. This phenomenon is called creaming. Creaming is one of the first signs of impending emulsion instability and should be taken seriously. Centrifugation can be used as a test method to predict creaming. The compositions can be heated to 50° C. (122° F.) and centrifuged for thirty minutes at 3000 rpm. The resultant products can be inspected for signs of creaming. The compositions are expected to remain emulsified and not exhibit creaming.

Mechanical Shock Testing: In order to determine whether or not shipping movements may damage the cosmetic compositions and their packaging, mechanical shock test experiments can be conducted. Vibration testing on a vortex mixer can be performed for durations of 30 s, 1 min., and 5 min. The compositions are expected to retain their viscosities and emulsified states after the three experiment durations.

Example 3

Clinical Results

Figure 1B:
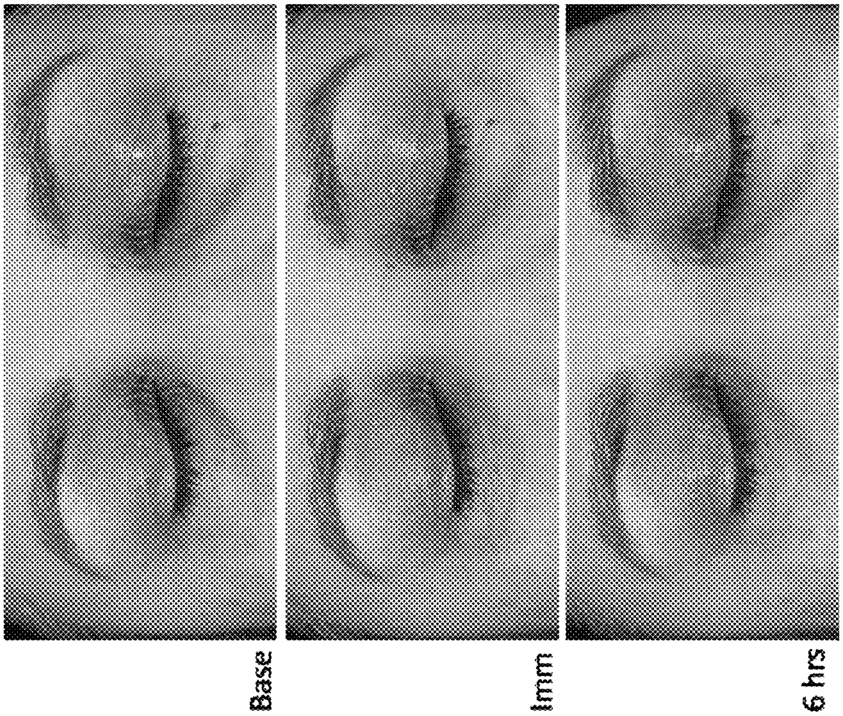

As shown by the before and after pictures in FIG. 1, a combination of sodium silicate, sodium polystyrene sulfonate, carrageenan, *Acacia senegal* gum-encapsulated xanthan gum, xanthan gum, and *Cyamopsis tetragonoloba* (guar) gum can reduce puffiness and/or crepiness, reduce under eye lines, and improve skin feel, soften skin, and attract and retain moisture around an eye area of a face. A formulation as disclosed above in Table 6 comprising a combination of sodium silicate, sodium polystyrene sulfonate, carrageenan, *Acacia senegal* gum-encapsulated xanthan gum, xanthan gum, and *Cyamopsis tetragonoloba* (guar) gum was applied to skin underneath and laterally outward of a lateral canthal region of the eye area of two clinical subjects' faces. Pictures were taken before (base), immediately after (Imm), and six hours (6 hrs) after application of the composition. A summary of clinical results obtained after treatment with the formulation according to Table 6 comprising a combination of sodium silicate, sodium polystyrene sulfonate, carrageenan, *Acacia senegal* gum-encapsulated xanthan gum, xanthan gum, and *Cyamopsis tetragonoloba* (guar) gum is found in Table 7, and the methods used to determine the properties of the ingredients are provided below.

TABLE 7

| | Puffiness | | Under Eye Lines | | Crepiness | |
|---|---|---|---|---|---|---|
| | Immediate | 6 Hour | Immediate | 6 Hour | Immediate | 6 Hour |
| Mean Clinical Grade A | 1.41 | 1.30 | 0.88 | 0.63 | 0.96 | 0.68 |
| Percent Change | 27% | 25% | 21% | 15% | 24% | 17% |
| Percent of Panelists | 96% | 86% | 79% | 75% | 82% | 75% |

Clinical Grading of Puffiness in the Under-Eye Area Assay: Clinical grading of puffiness in the under-eye area can be assessed via a ten-point analog numerical scale where (0) represents no puffiness and (9) represents severe puffiness under the eye area, very noticeable and very pronounced. Evaluations may be independently made by two or more clinicians and averaged.

Clinical Grading of Fine Lines & Wrinkles in the Under-Eye Area Assay: Clinical grading of fine lines & wrinkles in the under-eye area can be assessed via a ten-point analog numerical scale where (0) represents no fine lines visible and (9) represents severe deep lines & wrinkles present. Evaluations may be independently made by two or more clinicians and averaged.

Clinical Grading of Crepiness in the Under-Eye Area Assay: Clinical grading of crepiness in the under-eye area can be assessed via a ten-point analog numerical scale where (0) represents no crepiness and (9) represents severe crepiness under the eye area, very noticeable lines and very pronounced. Evaluations may be independently made by two or more clinicians and averaged.

Example 4

Additional Assays

Assays that can be used to determine the efficacy of any one of the ingredients or any combination of ingredients or compositions having said combination of ingredients disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

Elastin Stimulation Assay: Elastin is a connective tissue protein that helps skin resume shape after stretching or contracting. Elastin is also an important load-bearing protein used in places where mechanical energy is required to be stored. Elastin is made by linking many soluble tropoelastin protein molecules, in a reaction catalyzed by lysyl oxidase. Elastin secretion and elastin fibers may be monitored in cultured human fibroblasts by a direct ELISA sandwich method and analyzed using the Meso Scale Discovery system SECTOR 2400 Imaging system.

Laminin and Fibronectin Stimulation Assay: Laminin and fibronectin are major proteins in the dermal-epidermal junction (DEJ) (also referred to as the basement membrane). The DEJ is located between the dermis and the epidermis interlocks forming fingerlike projections called rete ridges. The cells of the epidermis receive their nutrients from the blood vessels in the dermis. The rete ridges increase the surface area of the epidermis that is exposed to these blood vessels and the needed nutrients. The DEJ provides adhesion of the two tissue compartments and governs the structural integrity of the skin. Laminin and fibronectin are two structural glycoproteins located in the DEJ. Considered the glue that holds the cells together, laminin and fibronectin are secreted by dermal fibroblasts to help facilitate intra- and inter-cellular adhesion of the epidermal calls to the DEJ.

Laminin and fibronectin secretion may be monitored by quantifying laminin and fibronectin in cell supernatants of cultured human fibroblasts treated for 3 days with culture medium with or without 1.0% final concentration of the test ingredient(s). Following incubation, laminin and fibronectin content may be measured using immunofluorescent antibodies directed against each protein in an enzyme linked immuno-sorbant assay (ELISA).

ORAC Assay: Oxygen Radical Absorption (or Absorbance) Capacity (ORAC) of any one of the active ingredients, combination of ingredients, or compositions having said combinations disclosed in the specification can also be assayed by measuring the antioxidant activity of such ingredients or compositions. Antioxidant activity indicates a capability to reduce oxidizing agents (oxidants). This assay quantifies the degree and length of time it takes to inhibit the action of an oxidizing agent, such as oxygen radicals, that are known to cause damage to cells (e.g., skin cells). The ORAC value of any one of the active ingredients, combination of ingredients, or compositions having said combinations disclosed in the specification can be determined by methods known to those of ordinary skill in the art (see U.S. Publication Nos. 2004/0109905 and 2005/0163880; and commercially available kits such as Zen-Bio ORAC Antioxidant Assay kit (#AOX-2)). The Zen-Bio ORAC Antioxidant Assay kit measures the loss of fluorescein fluorescence over time due to the peroxyl-radical formation by the breakdown of AAPH (2,2'-axobis-2-methyl propanimidamide, dihydrochloride). Trolox, a water soluble vitamin E analog, serves as positive control inhibition fluorescein decay in a dose dependent manner.

Matrix Metalloproteinase 1 Enzyme Activity (MMP1) Assay: An in vitro matrix metalloprotease (MMP) inhibition assay. MMPs are extracellular proteases that play a role in many normal and disease states by virtue of their broad substrate specificity. MMP1 substrates include collagen IV. The Molecular Probes Enz/Chek Gelatinase/Collagenase Assay kit (#E12055) utilizes a fluorogenic gelatin substrate to detect MMP1 protease activity. Upon proteolytic cleavage, bright green fluorescence is revealed and may be monitored using a fluorescent microplate reader to measure enzymatic activity.

The Enz/Chek Gelatinase/Collagenase Assay kit (#E12055) from Invitrogen is designed as an in vitro assay to measure MMP1 enzymatic activity. The active ingredients, any one of the combination of ingredients, or compositions having said combinations disclosed in the specification can be assayed. The assay relies upon the ability of purified MMP1 enzyme to degrade a fluorogenic gelatin substrate. Once the substrate is specifically cleaved by MMP1 bright green fluorescence is revealed and may be monitored using a fluorescent microplate reader. Test materials are incubated in the presence or absence of the purified enzyme and substrate to determine their protease inhibitor capacity.

Cyclooxygenase (COX) Assay: An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. The Colormetric COX (ovine) Inhibitor screening assay (#760111, Cayman Chemical) can be used to analyze the effects of each of the active ingredients, any one of the combination of ingredients, or compositions having said combinations disclosed in the specification on the activity of purified cyclooxygnase enzyme (COX-1 or COX-2). According to manufacturer instructions, purified enzyme, heme and test extracts can be mixed in assay buffer and incubated with shaking for 15 min at room temperature. Following incubation, arachidonic acid and colorimetric substrate can be added to initiate the reaction. Color progression can be evaluated by colorimetric plate reading at 590 nm. The percent inhibition of COX-1 or COX-2 activity can be calculated compared to non-treated controls to determine the ability of test extracts to inhibit the activity of purified enzyme.

Lipoxygenase (LO) Assay: An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives that are subsequently converted to leukotrienes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid. The Colorimetric LO Inhibitor screening kit (#760700, Cayman Chemical) can be used to determine the ability of each of the active ingredients, any one of the combination of ingredients, or compositions having said combinations disclosed in the specification to inhibit enzyme activity. Purified 15-lipoxygenase and test ingredients can be mixed in assay buffer and incubated with shaking for 10 min at room temperature. Following incubation, arachidonic acid can be added to initiate the reaction and the mixtures can be incubated for an additional 10 min at room temperature. Colorimetric substrate can be added to terminate catalysis and color progression can be evaluated by fluorescence plate reading at 490 nm. The percent inhibition of lipoxygenase activity can be calculated compared to non-treated controls to determine the ability of each of the active ingredients, any one of the combination of ingredients, or compositions having said combinations disclosed in the specification to inhibit the activity of purified enzyme.

Elastase Assay: ENZCHEK® Elastase Assay (Kit #E-12056) from Molecular Probes (Eugene, Oregon USA) can be used as an in vitro enzyme inhibition assay for measuring inhibition of elastase activity for each of the active ingredients, any one of the combination of ingredients, or compositions having said combinations disclosed in the specification. The EnzChek kit contains soluble bovine neck ligament elastin that can be labeled with dye such that the conjugate's fluorescence can be quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide, N-methoxysuccinyl-Ala-Ala-Pro-Val-chloromethyl ketone, can be used as a selective, collective inhibitor of elastase when utilizing the EnzChek Elastase Assay Kit for screening for elastase inhibitors.

Oil Control Assay: An assay to measure reduction of sebum secretion from sebaceous glands and/or reduction of sebum production from sebaceous glands can be assayed by using standard techniques known to those having ordinary skill in the art. In one instance, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

Erythema Assay: An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with the active ingredients, any one of the combination of ingredients, or compositions having said combinations disclosed in the specification. Repeat measurements can be taken at regular intervals to determine the formula's ability to reduce redness and irritation.

Skin Moisture/Hydration Assay: Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance. Each of the active ingredients, any one of the combination of ingredients, or compositions having said combinations disclosed in the specification can be assayed according to this process.

Skin Clarity and Reduction in Freckles and Age Spots Assay: Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether each of the active ingredients, any one of the combination of ingredients, or compositions having said combinations disclosed in the specification is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin Dryness, Surface Fine Lines, Skin Smoothness, and Skin Tone Assay: Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay: Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations may be independently made by two clinicians and averaged.

Clinical Grading of Skin Smoothness Assay: Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations may be independently made by two clinicians and averaged.

Skin Smoothness and Wrinkle Reduction Assay With Methods Disclosed in Packman et al. (1978): Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score can be obtained by multiplying a number factor times a depth/width/length factor. Scores are obtained for the eye area and mouth area (left and right sides) and added together as the total wrinkle score.

Skin Firmness Assay with a Hargens Ballistometer: Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer: Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas: The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subject's face and analyzing the replicas image using a computer image analysis system. Replicas can be taken from the eye area and the neck area, and photographed with a digital camera using a low angle incidence lighting. The digital images can be analyzed with an image processing program.

Surface Contour of the Skin Assay with a Profilometer/Stylus Method: The surface contour of the skin can be measured by using the profilometer/stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fixed axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt is the maximum vertical distance between the highest peak and lowest trough, and Rz is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

MELANODERM™ Assay: In other non-limiting aspects, the efficacy of each of the active ingredients, any one of the combination of ingredients, or compositions having said combinations disclosed in the specification can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing each of the active ingredients, any one of the combination of ingredients, or compositions having said combinations disclosed in the specification or with the base alone as a control. Alternatively, an untreated sample of the skin analog can be used as a control.

Production of Filaggrin: Changes in the production of filaggrin in keratinocytes due to each of the active ingredients, any one of the combination of ingredients, or compositions having said combinations disclosed in the specification can be measured. Filaggrin is the precursor to Natural Moisturizing Factor (NMF) in the skin. Increased NMF increases the moisture content of the skin. Filaggrin production in treated and non-treated keratinocytes can be determined using a bioassay that analyzes filaggrin concentration in keratinocyte cell lysates. A non-limiting example of a bioassay that can be used to quantify filaggrin production is the PROTEINSIMPLE® SIMON™ western blotting protocol. For each sample, normal human epidermal keratinocytes (NHEK) are grown in EPI-200—Mattek EPILIFE® growth media with calcium from Life Technologies (M-EP-500-CA). NHEK are incubated in growth medium overnight at 37° C. in 5% $CO_2$ prior to treatment. NHEK are then incubated in growth medium with 1% test compound/extract or no compound/extract (negative control) for 24 to 36 hours. The NHEK can then be washed, collected, and stored on ice or colder until lysed on ice using a lysis buffer and sonication. The protein concentrations of the samples can be determined and used to normalize the samples. The lysates can be stored at −80° C. until use in the quantification assay.

The PROTEINSIMPLE® SIMON™ western blotting bioassay assay employs a quantitative western blotting immunoassay technique using an antibody specific for filaggrin to quantitatively detect filaggrin in the test samples. Cell samples are lysed and normalized for protein concentration. Normalized samples and molecular weight standards can then be loaded and ran on a denatured protein separation gel using capillary electrophoresis. The proteins in the gel are immobilized and immunoprobed using a primary antibody specific for filaggrin. The immobilized proteins can then be immunoprobed with an enzyme-linked detection antibody that binds the primary antibody. A chemiluminescent substrate solution can then be added to the immobilized proteins to allow chemiluminescent development in proportion to the amount of filaggrin bound in the immobilization. The chemiluminescent development is stopped at a specific time and the intensity of the chemiluminescent signal can be measured and compared to positive and negative controls.

Production of Occludin: Changes in the production of occludin in keratinocytes due to each of the active ingredients, any one of the combination of ingredients, or compositions having said combinations disclosed in the specification can be measured. Occludin is a protein critical to the formulation of tight junctions and the skin's moisture barrier function. A non-limiting example of how occludin production in treated and non-treated keratinocytes can be determined is by the use of a bioassay that analyzes occludin concentration in keratinocyte cell lysates. The bioassay can be performed using PROTEINSIMPLE® SIMON™ western blotting protocol. For the samples, adult human epidermal keratinocytes (HEKa) from Life Technologies (C-005-5C) can be grown at 37° C. and 5% $CO_2$ for 24 hours in Epilife growth media with calcium from Life Technologies (M-EP-500-CA) supplemented with Keratinocyte Growth Supplement (HKGS) from Life Technologies (S-101-5). HEKa are then incubated in growth medium with test compound/extract, no compound/extract for negative control, or with 1 mM $CaCl_2$ for positive control for 24 to 48 hours. The HEKa are then washed, collected, and stored on ice or colder until lysed on ice using a lysis buffer and sonication. The protein concentrations of the samples can be determined and used to normalize the samples. The lysates are stored at −80° C. until use in the bioassay.

The PROTEINSIMPLE® SIMON™ western blotting bioassay assay employs a quantitative western blotting immunoassay technique using an antibody specific for occludin to quantitatively detect occludin in the test samples. Cell samples are lysed and normalized for protein concentration. Normalized samples and molecular weight standards are then loaded and ran on a denatured protein separation gel using capillary electrophoresis. The proteins in the gel are then immobilized and immunoprobed using a primary antibody specific for occludin. The immobilized proteins are immunoprobed with an enzyme-linked detection antibody that binds the primary antibody. A chemiluminescent substrate solution is then added to the immobilized proteins to allow chemiluminescent development in proportion to the amount of occludin bound in the immobilization. The chemiluminescent development can be stopped at a specific time and the intensity of the chemiluminescent signal can be measured and compared to positive and negative controls.

Keratinocyte Monolayer Permeability: Changes in the permeability of a keratinocyte monolayer due to each of the active ingredients, any one of the combination of ingredients, or compositions having said combinations disclosed in the specification can be measured. Keratinocyte monolayer permeability is a measure of skin barrier integrity. Keratinocyte monolayer permeability in treated and non-treated keratinocytes can be determined using, as a non-limiting example, the In Vitro Vascular Permeability assay by Millipore (ECM642). This assay analyzes endothelial cell adsorption, transport, and permeability. Briefly, adult human epidermal keratinocytes from Life Technologies (C-005-5C) can be seeded onto a porous collagen-coated membrane within a collection well. The keratinocytes are then incubated for 24 hours at 37° C. and 5% $CO_2$ in Epilife growth media with calcium from Life Technologies (M-EP-500-CA) supplemented with Keratinocyte Growth Supplement (HKGS) from Life Technologies (S-101-5). This incubation time allows the cells to form a monolayer and occlude the membrane pores. The media is then replaced with fresh media with (test sample) or without (non-treated control) test compounds/extracts and the keratinocytes are incubated for an additional 48 hours at 37° C. and 5% $CO_2$. To determine permeability of the keratinocyte monolayer after incubation with/without the test compound/extract, the media is replaced with fresh media containing a high molecular weight Fluorescein isothiocyanate (FITC)-Dextran and the keratinocytes are incubated for 4 hours at 37° C. and 5% $CO_2$. During the 4 hours incubation, FITC can pass through the keratinocytes monolayer and porous membrane into the collection well at a rate proportional to the monolayer's permeability. After the 4 hour incubation, cell viability and the content of FITC in the collection wells can be determined. For the FITC content, the media in the collection well is collected and fluorescence of the media determined at 480 nm (Em) when excited at 520 nm. Percent permeability and percent change in comparison to the non-treated controls can be determined by the following equations: Percent Permeability=((Mean Ex/Em of test sample)/Mean Ex/Em untreated control)*100; Percent Change=Percent Permeability of test sample−Percent Permeability of untreated control.

Production of Hyaluronic Acid: Changes in the production of hyaluronic acid in human dermal fibroblasts due to each of the active ingredients, any one of the combination of ingredients, or compositions having said combinations disclosed in the specification can be measured. HA is a polysaccharide involved in stabilization of the structure of the matrix and is involved in providing turgor pressure to tissue and cells. As one non-limiting example, HA production in treated and non-treated adult human dermal fibroblasts (HDFa) cells can be determined using the Hyaluronan DuoSet ELISA kit from R&D Systems (DY3614). In this assay, for production of samples, subconfluent HDFa cells from Cascade Biologics (C-13-5C) are incubated at 37° C. and 10% $CO_2$ in starvation medium (0.15% fetal bovine serum and 1% Penicillin Streptomycin solution in Dulbecco's Modified Eagle Medium) for 72 hours prior to treatment. The cells are then incubated with fresh starvation medium with either test compound, positive control (phorbol 12-myristate 13-acetate from Sigma-Aldrich (P1585) and platelet derived growth factor from Sigma-Aldrich (P3201)), or no additive for 24 hours. Media is then collected and frozen at −80° C. until use in the ELISA assay.

Briefly, the ELISA assay employs a quantitative sandwich enzyme immunoassay technique whereby a capture antibody specific for HA can be pre-coated onto a microplate. Standards and media from treated and untreated cells are pipetted into the microplate wells to enable any HA present to be bound by the immobilized antibody. After washing away any unbound substances, an enzyme-linked detection antibody specific for HA is added to the wells. Following a wash to remove any unbound antibody-enzyme reagent, a substrate solution is added to the wells to allow color development in proportion to the amount of HA bound in the initial step. The color development is stopped at a specific time and the intensity of the color at 450 nm can be measured using a microplate reader.

Inhibition of Hyaluronidase Activity: Changes in the activity of hyaluronidase due to each of the active ingredients, any one of the combination of ingredients, or compositions having said combinations disclosed in the specification can be measured. Hyaluronidase is an enzyme that degrades HA. HA is a polysaccharide involved in stabilization of the structure of the matrix and is involved in providing turgor pressure to tissue and cells. As one non-limiting example, hyaluronidase activity can be determined using an in vitro protocol modified from Sigma-Aldrich protocol #EC 3.2.1.35. Briefly, hyaluronidase type 1-S from Sigma-Aldrich (H3506) is added to microplate reaction wells containing test compound or controls. Tannic acid can be used as a positive control inhibitor, no test compound can be added for the control enzyme, and wells with test compound or positive control but without hyaluronidase can be used as a background negative control. The wells are incubated at 37° C. for 10 minutes before addition of substrate (HA). Substrate is added and the reactions incubated at 37° C. for 45 minutes. A portion of each reaction solution is then transferred to and gently mixed in a solution of sodium acetate and acetic acid pH 3.75 to stop that portion of the reaction (stopped wells). The stopped wells and the reaction wells should both contain the same volume of solution after addition of the portion of the reaction solution to the stopped wells. Both the reaction wells and the stopped wells are incubated for 10 minutes at room temperature. Absorbance at 600 nm is then measured for both the reaction wells and the stopped wells. Inhibition can be calculated using the following formulas: Inhibitor (or control) activity=(Inhibitor stopped wells absorbance at 600 nm−inhibitor reaction wells absorbance at 600 nm); Initial activity=control enzyme absorbance at 600 nm; Percent Inhibition=[(Initial activity/Inhibitor Activity)*100]−100.

Peroxisome Proliferator-Activated Receptor Gamma (PPAR-γ) Activity: Changes in the activity of PPAR-γ due to each of the active ingredients, any one of the combination of ingredients, or compositions having said combinations disclosed in the specification can be measured. PPAR-γ is a receptor critical for the production of sebum. As one non-limiting example, the activity of PPAR-γ can be determined using a bioassay that analyzes the ability of a test compound or composition to inhibit binding of a ligand. Briefly, fluorescent small-molecule pan-PPAR ligand, FLUORMONE™ Pan-PPAR Green, available from Life Technologies (PV4894), can be used to determine if test compounds or compositions are able to inhibit binding of the ligand to PPAR-γ. The samples wells include PPAR-γ and fluorescent ligand and either: test compound or composition (test); a reference inhibitor, rosiglitazone (positive control); or no test compound (negative control). The wells are incubated for a set period of time to allow the ligand opportunity to bind the PPAR-γ. The fluorescence polarization of each sample well can then be measured and compared to the negative control well to determine the percentage of inhibition by the test compound or composition.

Cytokine array: Human epidermal keratinocytes are cultured to 70-80% confluency. The media in the plate is aspirated and 0.025% trypsin/EDTA is added. When the cells are rounded, the culture dish is gently tapped to release the cells. The trypsin/EDTA containing cells are removed from the culture dish and neutralized. Cells are centrifuged for 5 min. at 180×g to form a pellet of cells. The supernatant is aspirated. The resulting pellet is resuspended in EPILIFE™ media (Cascade Biologics). The cells are seeded in 6-well plates at approximately 10-20% confluency. After the cells are approximately 80% confluent, the media is aspirated and 1.0 ml of EPILIFE™, along with phorbol 13-Myristate 12-acetate ("PMA") (a known inducer of inflammation) and the test composition dilutions are added to two replicate wells (i.e., 1.0% (100 μl of 100× stock) and 0.1% (10 μl of 100× stock) test compositions are diluted into a final volume of 1 ml EpiLife Growth Medium). The media is gently swirled to ensure adequate mixing. In addition, 1.0 ml of EPILIFE™ is added to the control wells, with and without additional PMA. The plates are then incubated at 37±1° C. and 5.0±1% $CO_2$ for approximately 5 hours after dosing. Following this 5-hour incubation, all media is collected in conical tubes and frozen at −70° C.

For analysis, a 16-pad hybridization chamber is attached to 16-pad FAST slides arrayed in triplicate with 16 anti-cytokine antibodies plus experimental controls (Whatman BioSciences), and the slides are placed into a FASTFrame (4 slides per frame) for processing. Arrays are blocked for 15 min. at room temperature using 70 ml S&S Protein Array Blocking buffer (Whatman Schleicher and Scheull). Blocking buffer is removed and 70 ml of each supernatant sample is added to each array. Arrays are incubated for 3 hours at room temperature with gentle agitation. Arrays are washed 3 times with TBS-T. Arrays are treated with 70 ml of an antibody cocktail, containing one biotinylated antibody corresponding to each of the arrayed capture antibodies. Arrays are incubated for 1 hour at room temperature with gentle agitation. Arrays are washed 3 times with TBS-T. Arrays are incubated with 70 ml of a solution containing streptavidin-Cy5 conjugate for 1 hour at room temperature with gentle agitation. Arrays are washed 3 times with TBS-T, quickly rinsed in de-ionized water, and dried.

Slides can be imaged in a Perkin-Elmer ScanArray 4000 confocal fluorescent imaging system. Array images can be saved and analyzed using Imaging Research ArrayVision software. Briefly, spot intensities are determined by subtracting background signal. Spot replicates from each sample condition can be averaged and then compared to the appropriate controls.

Endothelial Tube Formation: Endothelial tube formation is involved in angiogenesis and micro-vessel capillary formation. Capillary formation and angiogenesis may contribute to redness and rosacea of the skin. The ability for endothelial cells to form tubes in the presence or absence of test extracts and compounds may be determined using a capillary tubule disruption assay with pre-formed primary human umbilical vein endothelial cells (HUVEC) in a cell culture system.

Briefly, HUVECs are cultured in vitro on Extracellular Matrix, which stimulates the attachment and tubular morphogenesis of endothelial cells to form capillary-like lumen structures. These in vitro formed capillary tubules are similar to human blood vessel capillaries in many aspects. The capillary tube assay is based on this phenomenon and is used for evaluation of potential vasculature targeting agents.

HUVEC cultures are grown in a 5% $CO_2$ 37° C. cell incubator. The full growth medium for HUVECs is Endothelial Cell Basal Medium (EBM) supplemented with 2% fetal bovine serum (FBS), 12 μg/ml bovine brain extract, 1 μg/ml hydrocortisone, and 1 μg/ml GA-1000 (gentamicin-amphotericin). HUVEC cultures between passage 3 and 8 may be used for all assay experiments.

HUVECs are pre-labeled with fluorescent agent Calcein AM and seeded in Extracellular Matrix coated 96-well culture plate with their full growth medium. After about four hours of the morphogenesis process, the endothelial capillary tubes should be formed. Then, test agent in designed doses of 50 μl volume is applied into the formed capillary tubule cultures as treatment conditions. The no-treatment controls can be added with vehicle of test agents. Sutent, a FDA approved anti-angiogenic drug one concentration can be included as assay performance control. After about six hours of treatment, the endothelial tubule morphology in each well is examined by microscopy, imaged, and the capillary disrupting activities under treatment conditions can be quantitatively analyzed. Each test conditions can be conducted in duplicate wells, including controls.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method of stabilizing a skin care composition comprising adding attapulgite clay, hydroxyethyl acrylate/sodium acryloyldimethyl taurate copolymer, and *Acacia senegal* gum-encapsulated xanthan gum to the skin care composition to form a stabilized skin care composition,
- wherein the stabilized skin care composition is provided as an aqueous mineral suspension,
- wherein the stabilized skin care composition does not include any one of or any combination of:
  - hectorite;
  - an effective amount of a UV absorption agent to provide a sunblock;
  - an effective amount of a UV reflecting agent to provide a sunblock; or
  - polyvinylpyrrolidone (PVP), and
- wherein the stabilized skin care composition is stable after one or more freeze and thaw cycles.

2. The method of claim 1, wherein the composition comprises from about 0.01 to 10% by weight of attapulgite clay, from about 0.001 to 1% by weight of hydroxyethyl acrylate/sodium acryloyldimethyl taurate copolymer, and from about 0.05 to 5% by weight of *Acacia senegal* gum-encapsulated xanthan gum.

3. The method of claim 1, further comprising adding magnesium aluminum silicate, sodium polystyrene sulfonate, and xanthan gum to the skin care composition.

4. The method of claim 3, wherein the composition comprises from about 0.2 to 20% by weight of magnesium aluminum silicate, from about 0.1 to 10% by weight of sodium polystyrene sulfonate, and from about 0.02 to 2% by weight of xanthan gum.

5. The method of claim 1, further comprising adding one or more of sodium silicate, an alkyl glycol, carrageenan, mica, titanium dioxide, iron oxides, EDTA, ethylhexylglycerin, phenoxyethanol, tocopherol, isohexadecane, polysorbate 60, sodium sulfate, *Cyamopsis tetragonoloba* (guar) gum, and sorbitan isostearate to the skin care composition.

6. The method of claim 5, wherein the composition comprises from about 0.1 to 10% by weight of sodium silicate, from about 1.5 to 2.5% by weight of alkyl glycol, from about 0.02 to 2% by weight of carrageenan, from about 0.01 to 1% by weight of mica, from about 0.01 to 1% by weight of titanium dioxide, from about 0.01 to 1% by weight of iron oxides, from about 0.01 to 1% by weight of EDTA, from about 0.01 to 1% by weight of ethylhexylglycerin, from about 0.05 to 5% by weight of phenoxyethanol, from about 0.000001 to 0.0001% by weight of tocopherol, from about 0.001 to 1% by weight of isohexadecane, from about 0.001 to 1% by weight of polysorbate 60, from about 0.01 to 1% by weight of sodium sulfate, from about 0.01 to 1% by weight of *Cyamopsis tetragonoloba* (guar) gum, and from about 0.0001 to 0.01% by weight of sorbitan isostearate.

7. A method of moisturizing skin around an eye area of a face, the method comprising the step of topically applying a composition comprising sodium silicate, sodium polystyrene sulfonate, carrageenan, *Acacia senegal* gum-encapsulated xanthan gum, xanthan gum, and *Cyamopsis tetragonoloba* (guar) gum around the eye area of a face,
- wherein the composition further comprises attapulgite clay and hydroxyethyl acrylate/sodium acryloyldimethyl taurate copolymer; and/or magnesium aluminum silicate,
- wherein the composition does not include any one of or any combination of:
  - hectorite;
  - an effective amount of a UV absorption agent to provide a sunblock;
  - an effective amount of a UV reflecting agent to provide a sunblock; or
  - polyvinylpyrrolidone (PVP),
- wherein the skin around the eye area of the face is in need of moisture,
- wherein application of the composition attracts and retains moisture around the eye area of the face, and
- wherein applying the composition to the skin around an eye area of a face reduces puffiness, improves skin feel, and/or softens skin.

8. The method of claim 7, wherein the composition comprises from about 0.1 to 10% by weight of sodium silicate, from about 0.1 to 10% by weight of sodium polystyrene sulfonate, from about 0.02 to 2% by weight of carrageenan, from about 0.05 to 5% by weight of *Acacia senegal* gum-encapsulated xanthan gum, from about 0.02 to 2% by weight of xanthan gum, and from about 0.01 to 1% by weight of *Cyamopsis tetragonoloba* (guar) gum.

9. The method of claim 7, wherein the composition comprises:
- from about 0.01 to 10% by weight of attapulgite clay and from about 0.001 to 1% by weight of hydroxyethyl acrylate/sodium acryloyldimethyl taurate copolymer; and/or from about 0.2 to 20% by weight of magnesium aluminum silicate.

10. The method of claim 7, wherein the composition further comprises one or more of: an alkyl glycol, mica, titanium dioxide, iron oxides, EDTA, ethylhexylglycerin, phenoxyethanol, tocopherol, isohexadecane, polysorbate 60, and sorbitan isostearate.

11. The method of claim 10, wherein the composition comprises from about 1.5 to 2.5% by weight of alkyl glycol, from about 0.01 to 1% by weight of mica, from about 0.01 to 1% by weight of titanium dioxide, from about 0.01 to 1% by weight of iron oxides, from about 0.01 to 1% by weight of EDTA, from about 0.01 to 1% by weight of ethylhexylglycerin, from about 0.05 to 5% by weight of phenoxyethanol, from about 0.000001 to 0.0001% by weight of tocopherol, from about 0.001 to 1% by weight of isohexadecane, from about 0.001 to 1% by weight of polysorbate 60, and from about 0.0001 to 0.01% by weight of sorbitan isostearate.

12. The method of claim 1, wherein the stabilized skin care composition does not include more than 0.12 wt. % of a UV absorption agent, a UV reflecting agent, or a combination of UV absorption and UV reflecting agents.

13. The method of claim 7, wherein the composition does not include more than 0.12 wt. % of a UV absorption agent, a UV reflecting agent, or a combination of UV absorption and UV reflecting agents.

14. The method of claim 1, wherein the stabilized skin care composition does not include more than 0.12 wt. % of titanium dioxide, iron oxide, or a combination of titanium dioxide and iron oxide.

15. The method of claim 7, wherein the composition does not include more than 0.12wt. % of titanium dioxide, iron oxide, or a combination of titanium dioxide and iron oxide.

16. The method of claim 1, wherein the stabilized skin care composition does not include more than 0.12 wt. % of an inorganic UV absorption agent or a inorganic UV reflecting agent.

17. The method of claim 7, wherein the composition does not include more than 0.12 wt. % of an inorganic UV absorption agent or a inorganic UV reflecting agent.

* * * * *